(12) United States Patent
Kwak et al.

(10) Patent No.: US 8,431,241 B2
(45) Date of Patent: Apr. 30, 2013

(54) ORGANIC LIGHT-EMITTING DEVICE

(75) Inventors: Yoon-Hyun Kwak, Yongin (KR);
Seok-Hwan Hwang, Yongin (KR);
Young-Kook Kim, Yongin (KR);
Hye-Jin Jung, Yongin (KR); Jong-Hyuk Lee, Yongin (KR); Jin-O Lim, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 136 days.

(21) Appl. No.: 12/855,523

(22) Filed: Aug. 12, 2010

(65) Prior Publication Data

US 2011/0049486 A1    Mar. 3, 2011

(30) Foreign Application Priority Data

Sep. 2, 2009  (KR) .................. 10-2009-0082566

(51) Int. Cl.
*B03B 9/00* (2006.01)

(52) U.S. Cl.
USPC .......................................... 428/680; 428/917

(58) Field of Classification Search .................. 428/917, 428/690; 313/504, 506
See application file for complete search history.

(56) References Cited

U.S. PATENT DOCUMENTS

| | | | |
|---|---|---|---|
| 6,951,693 B2 * | 10/2005 | Hosokawa et al. | 428/690 |
| 2004/0096397 A1 | 5/2004 | Menchen et al. | |
| 2005/0089717 A1 * | 4/2005 | Cosimbescu et al. | 428/690 |
| 2006/0043858 A1 | 3/2006 | Ikeda et al. | |
| 2011/0031484 A1 | 2/2011 | Lee et al. | |
| 2011/0031485 A1 | 2/2011 | Kwak et al. | |

FOREIGN PATENT DOCUMENTS

| | | |
|---|---|---|
| JP | 02-085252 | 3/1990 |
| JP | 04-016851 | 1/1992 |
| JP | 04-016853 | 1/1992 |
| JP | 04-031868 | 2/1992 |
| JP | 4025136 B2 | 10/2007 |
| JP | 4041816 B2 | 2/2008 |
| JP | 2010-034450 | 2/2010 |
| JP | 2010-073987 | 4/2010 |
| JP | 2010-087408 | 4/2010 |
| JP | 2010-219302 | 9/2010 |
| JP | 2010-225861 | 10/2010 |
| JP | 2011-037831 | 2/2011 |
| JP | 2011-037854 | 2/2011 |
| JP | 2012-510988 | 5/2012 |
| JP | 2012-520872 | 9/2012 |
| KR | 10-2008-0086844 A | 9/2008 |
| KR | 10-2008-0014812 A | 12/2008 |
| KR | 10-2008-0114784 A | 12/2008 |
| WO | WO 2010/064871 A1 | 6/2010 |
| WO | WO 2010/107244 A2 | 9/2010 |

OTHER PUBLICATIONS

European Search Report dated Jan. 17, 2011, for corresponding European Patent application 10174612.1.

(Continued)

*Primary Examiner* — Howard Weiss
*Assistant Examiner* — Steven Rao
(74) *Attorney, Agent, or Firm* — Christie, Parker & Hale, LLP

(57) ABSTRACT

Embodiments of the present invention are directed to a heterocyclic compound and an organic light-emitting device including the heterocyclic compound. The organic light-emitting devices using the heterocyclic compounds have high-efficiency, low driving voltages, high brightness and long lifespans.

18 Claims, 1 Drawing Sheet

OTHER PUBLICATIONS

Marzinzik, A.L., et al., *Structural chemistry of polycyclic heteroaromatic compounds. Part 9. Photoelectron spectra and electronic structures of anellated carbazoles. Extension of Clar's aromatic sextet model to hetarenes*, Journal of Molecular Structure, vol. 375, Jan. 1, 1996, pp. 117-126, XP 002612195.

KIPO Notice of Allowance dated Sep. 27, 2012, for Korean priority Patent application 10-2009-0082566, (5 pages).

Japanese Office action dated Oct. 30, 2012, for corresponding Japanese Patent application 2010-193061, (6 pages).

Zander, M, et al., *Synthesen von 9-Methyl-2.3;6.7-dibenzo-carbazol, 9-Methyl 2.3;5.6-dibenzo-carbazol und Dinaphtho-[2'.3':2.3;2". 3":5.6]-carbazol.*, Chemische Berichte, vol. 98, No. 9, Sep. 1, 1965, pp. 2814-2821, XP-002612191.

Zander, M, et al., *Innermolekulare Umlagerungen von anellierten Carbazolen*, Chemische Berichte, vol. 100, No. 8, Aug. 1, 1967, pp. 2649-2654, XP-002612192.

Zander, M. et al., *Beziehungen in den Ultraviolettspektren von höheranellierten Carbazolen and aromatischen Kohlenwasserstoffen*, Chemische Berichte, vol. 98, No. 2, Feb. 1, 1965, pp. 588-592, XP 002612193.

Zander, M. et al., *Synthese einiger Naphthocarbazole*, Chemische Berichte, vol. 96, No. 3, Mar. 1, 1963, pp. 699-706, XP-002612194.

Zander, M., *Zur Anwendung des äußeren Schweratom-Effekts in der Spektrofluorimetrie*, Zeitschrift For Analytische Chemie, vol. 263, No. 1, Jan. 1, 1973 , pp. 19-23, XP-002612196.

Jurié, A, et al., *Aromaticity in Bridged Heteroannulenes*, Journal of Heterocyclic Chemistry, Mar.-Apr. 1984, vol. 21, No. 2, pp. 273-282.

Catalán, J., *Spectrothermodynamic Relationship of Cationic vs. Anionic Species Derived from Protonation vs. Deprotonation of Pyrrolo-aza-Aromatic Bases in Homologous Series*, Journal of American Chemical Society, (2001), vol. 123, No. 48, pp. 11940-11944.

\* cited by examiner

| SECOND ELECTRODE |
|---|
| EIL |
| ETL |
| EML |
| HTL |
| HIL |
| FIRST ELECTRODE |

ORGANIC LIGHT-EMITTING DEVICE

CROSS-REFERENCE TO RELATED PATENT APPLICATION

This application claims priority to and the benefit of Korean Patent Application No. 10-2009-0082566 filed on Sep. 2, 2009 in the Korean Intellectual Property Office, the entire content of which is incorporated herein by reference.

BACKGROUND OF THE INVENTION

1. Field of the Invention

The present invention relates to heterocyclic compounds and organic light-emitting devices including the heterocyclic compounds.

2. Description of the Related Art

Organic light-emitting devices are self-emission type display devices, and have wide viewing angles, high contrast ratios, and short response times. Due to these characteristics, organic light-emitting devices are drawing much attention.

Light-emitting devices can be roughly classified into inorganic light-emitting devices which include emission layers containing inorganic compounds, and organic light-emitting devices which include containing organic compounds. Organic light-emitting devices have higher luminance, lower driving voltages, and shorter response times than inorganic light-emitting devices. In addition, organic light-emitting devices produce various colors. Thus, research has been conducted into organic light-emitting devices.

Typically, an organic light-emitting device has a stack structure including an anode, a cathode and an organic emission layer therebetween. However, a hole injection layer and/or a hole transport layer may be further stacked between the anode and the organic emission layer, and/or an electron transport layer may be further stacked between the organic emission layer and the cathode. In other words, an organic light-emitting device may have an anode/hole transport layer/organic emission layer/cathode stack structure, or an anode/hole transport layer/organic emission layer/electron transport layer/cathode stack structure.

As a material for forming the organic emission layer, an anthracene derivative may be used. However, organic light-emitting devices including known light-emitting materials do not have satisfactory life span, efficiency, or power consumption characteristics, thus leaving much room for improvement.

SUMMARY OF THE INVENTION

According to embodiments of the present invention, a heterocyclic compound has improved electrical characteristics, charge transporting capabilities and light-emission capabilities.

In some embodiments of the present invention, an organic light-emitting device includes the heterocyclic compound.

In other embodiments of the present invention, a flat panel display device includes the organic light-emitting device.

According to some embodiments of the present invention, an organic light-emitting device includes at least one layer containing the heterocyclic compound, where the at least one layer is formed using a wet process.

According to embodiments of the present invention, a heterocyclic compound includes compounds represented by Formula 1 below:

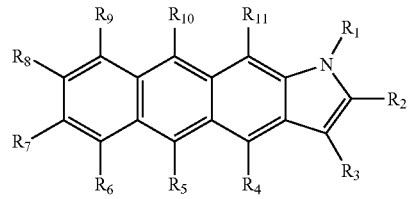

Formula 1

In Formula 1, each of $R_1$ through $R_{11}$ is independently selected from hydrogen atoms, heavy hydrogen atoms, substituted and unsubstituted $C_{10}$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{50}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_1$ through $R_{11}$ may optionally bond to each other, thereby forming an aromatic ring.

$R_1$ may be selected from unsubstituted and substituted monocyclic to tricyclic aryl groups. The unsubstituted monocyclic to tricyclic aryl groups may be selected from phenyl groups, naphthyl groups, biphenyl groups, terphenyl groups, anthracenyl groups, fluorenyl groups, and carbazolyl groups. The substituted monocyclic to tricyclic aryl groups may be selected from phenyl groups, naphthyl groups, biphenyl groups, terphenyl groups, anthracenyl groups, fluorenyl groups, and carbazolyl groups substituted with at least one substituent selected from $C_1$-$C_5$ alkyl groups, $C_1$-$C_5$ alkoxy groups, cyano groups, amine groups, phenoxy groups, phenyl groups and halogen groups.

$R_7$ may be selected from unsubstituted and substituted monocyclic to tricyclic aryl groups, and unsubstituted and substituted $C_{12}$-$C_{50}$ arylamine groups. The unsubstituted monocyclic to tricyclic aryl groups may be selected from phenyl groups, naphthyl groups, biphenyl groups, terphenyl groups, anthracenyl groups, fluorenyl groups and carbazolyl groups. The substituted monocyclic to tricyclic aryl groups may be selected from phenyl groups, naphthyl groups, biphenyl groups, terphenyl groups, anthracenyl groups, fluorenyl groups, and carbazolyl groups substituted with at least one substituent selected from $C_1$-$C_5$ alkyl groups, $C_1$-$C_5$ alkoxy groups, cyano groups, amine groups, phenoxy groups, phenyl groups, and halogen groups. The substituted $C_{12}$-$C_{50}$ arylamine groups may be selected from groups substituted with a substituent selected from $C_1$-$C_5$ alkyl groups, $C_1$-$C_4$ alkoxy groups, cyano groups, amine groups, phenoxy groups, phenyl groups, and halogen groups.

Each of $R_2$ and $R_3$ may independently be selected from methyl groups and phenyl groups.

Each of $R_5$ and $R_{10}$ may independently be selected from t-butyl groups, phenyl groups, naphthyl groups, and fluorenyl groups.

In some embodiments, the heterocyclic compound may include one of Compounds 11, 29, 43, 56, 74 and 82 below:

11

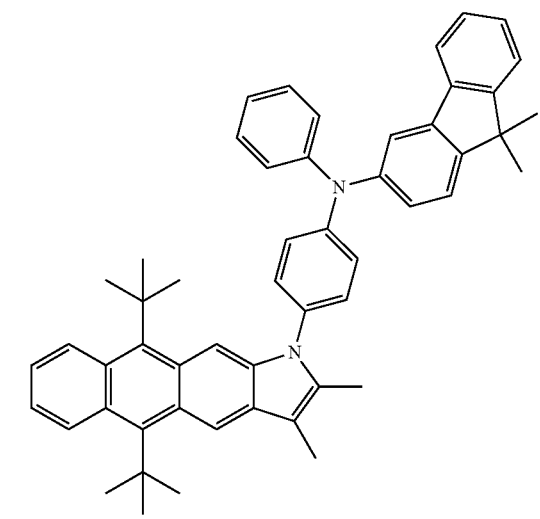

29

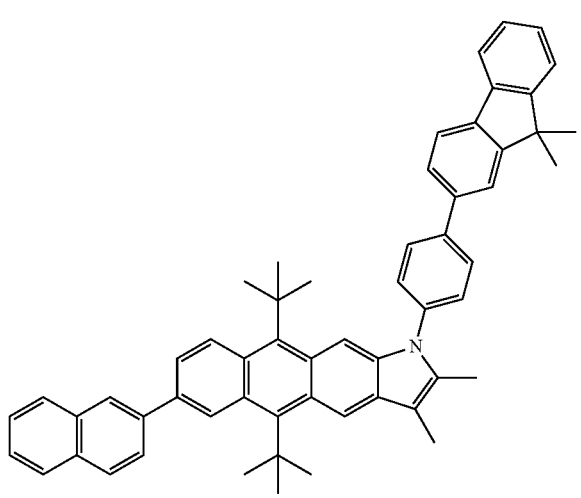

43

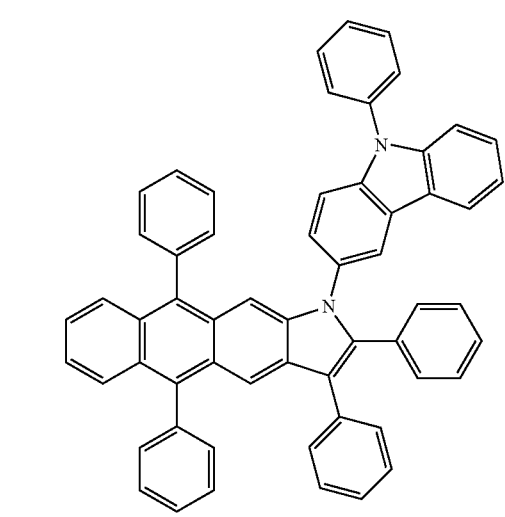

56

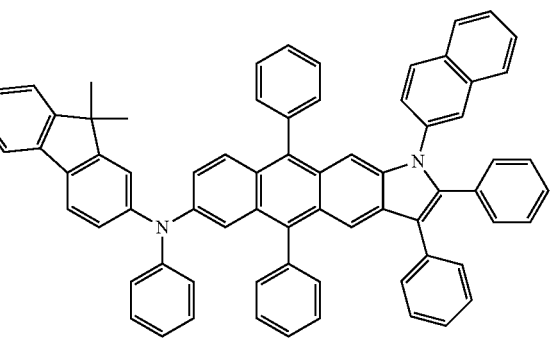

74

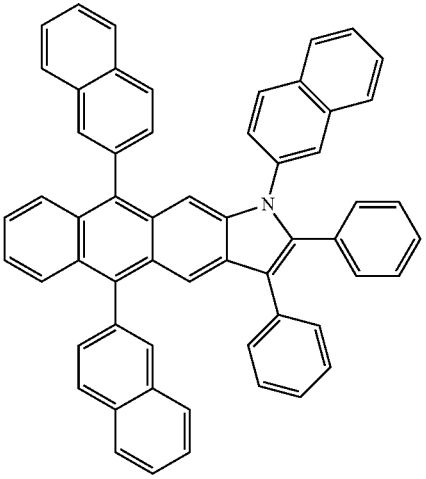

82

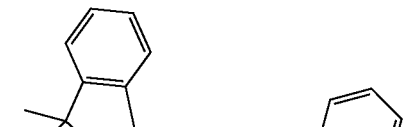
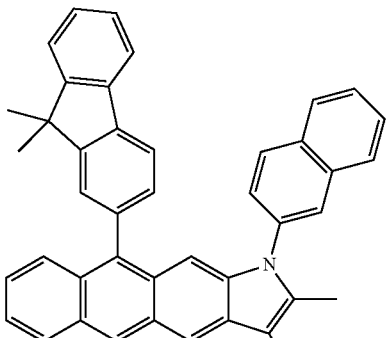
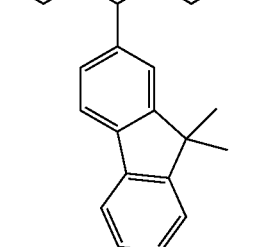

According to other embodiments of the present invention, an organic light-emitting device including a first electrode, a second electrode, and at least one organic layer between the first electrode and the second electrode. The at least one organic layer includes at least one layer including the heterocyclic compound.

The organic layer may include an electron injection layer or an electron transport layer.

The organic layer may include a single layer having both electron injection and electron transport capabilities.

The organic layer may include an emission layer.

The organic layer may include an emission layer, and the heterocylic compound may be used as a fluorescent or phosphorescent host.

The organic layer may include an emission layer, and the heterocylic compound may be used as a fluorescent dopant.

The organic layer may include an emission layer and an electron injection layer or an electron transport layer, and the emission layer may include an anthracene compound.

The organic layer may include an emission layer and an electron injection layer or an electron transport layer, and the emission layer may include an arylamine compound.

The organic layer may include an emission layer and an electron injection layer or an electron transport layer, and the emission layer may include a styryl compound.

The organic layer may include an emission layer, and an electron injection layer or an electron transport layer, and the emission layer may include a red emission layer, a green emission layer, a blue emission layer, or a white emission layer, each of which may include a phosphorescent compound.

The organic layer may include at least one layer selected from a hole injection layer, a hole transport layer, an electron blocking layer, an emission layer, a hole blocking layer, an electron transport layer, and an electron injection layer.

The organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode layer structure.

According to embodiments of the present invention, a flat panel display device includes the organic light-emitting device described above, where the first electrode of the organic light-emitting device is electrically connected to a source electrode or a drain electrode of a thin-film transistor.

According to other embodiments of the present invention, an organic light-emitting device includes a first electrode, a second electrode, and an organic layer between the first electrode and the second electrode. The organic layer includes at least one layer comprising the heterocyclic compound, which layer can be formed using a wet process.

BRIEF DESCRIPTION OF THE DRAWINGS

The above and other features and advantages of the present invention will become more apparent by reference to the following detailed description when considered in conjunction with the attached drawing in which:

FIG. 1 is a schematic diagram depicting the structure of an organic light-emitting device according to an embodiment of the present invention.

DETAILED DESCRIPTION OF THE INVENTION

The present invention will now be described with reference to the accompanying drawings, in which exemplary embodiments of the invention are shown.

A heterocyclic compound according to an embodiment of the present invention is represented by Formula 1 below:

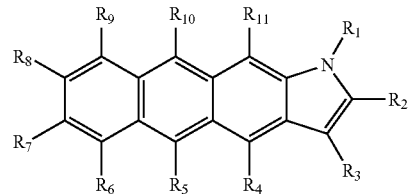

Formula 1

In Formula 1, each of $R_1$ through $R_{11}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{50}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_1$ through $R_{11}$ may optionally bond to each other, thereby forming an aromatic ring.

Anthracene derivatives have been as materials for an organic emission layer. For example, organic light-emitting devices have been manufactured using phenylanthracene dimers or trimers. However, such organic light-emitting devices have narrow energy gaps and lower blue-light color purity since two or three oligomeric species of anthracene are linked by conjugation. In addition, such compounds are highly vulnerable to oxidation and thus are liable to produce impurities, necessitating purification.

In an effort to address these drawbacks, organic light-emitting devices have been manufactured using anthracene compounds including naphthalene substituted for anthracene at the 1 and 9 positions, and devises have also been manufactured using diphenylanthracene compounds including an aryl group substituted for a phenyl group at the meta position. However, these organic light-emitting devices have lower light-emission efficiency.

In addition, organic light-emitting devices have been manufactured using a naphthalene-substituted monoanthracene derivative. However, the light-emission efficiency thereof is low (at about 1 cd/A), and thus such organic light-emitting devices are not suitable for practical use.

Furthermore, organic light-emitting devices have been manufactured using a phenylanthracene compound including an aryl substituent at the meta position. Such a compound has sufficient thermal resistance but low light-emission efficiency of about 2 cd/A. Thus, further improvement is required.

The heterocyclic compounds of Formula 1 according to embodiments of the present invention may be suitable as a material for an emission layer (EML) and/or an electron transport layer (ETL) or an electron injection layer (EIL) of an organic light-emitting device. The heterocyclic compounds of Formula 1 have high glass transition temperatures (Tg) or melting points due to the introduction of the heterocyclic group. Thus, the heterocyclic compounds have thermal resistance against Joule heat generated in an organic layer, between organic layers, or between an organic layer and a metallic electrode when light emission occurs, and are highly durable in high-temperature environments.

According to embodiments of the present invention, an organic light-emitting device manufactured using a heterocyclic compound of Formula 1 (which includes an anthracene group and an indole group fused thereto) has good durability when stored or operated. In addition, due to the introduction of a substituent such as a fluorene group, molecular films may be maintained in good condition, thereby improving the characteristics of the organic light-emitting device.

The substituents in the heterocyclic compound of Formula 1 will now be described. In Formula 1, $R_1$ may be selected from unsubstituted and substituted monocyclic to tricyclic aryl groups. The unsubstituted monocyclic to tricyclic aryl groups may be selected from phenyl groups, naphthyl groups, biphenyl groups, terphenyl groups, anthracenyl groups, fluorenyl groups, and carbazolyl groups The substituted monocyclic to tricyclic aryl groups may be selected from phenyl groups, naphthyl groups, biphenyl groups, terphenyl groups, anthracenyl groups, fluorenyl groups, and carbazolyl groups substituted with at least one substituent selected from $C_1$-$C_5$ alkyl groups, $C_1$-$C_5$ alkoxy groups, cyano groups, amine groups, phenoxy groups, phenyl groups and halogen groups.

$R_7$ may be selected from unsubstituted and substituted monocyclic to tricyclic aryl groups, and unsubstituted and substituted $C_{12}$-$C_{50}$ arylamine groups. The unsubstituted monocyclic to tricyclic aryl groups may be selected from phenyl groups, naphthyl groups, biphenyl groups, terphenyl groups, anthracenyl groups, fluorenyl groups and carbazolyl groups. The substituted monocyclic to tricyclic aryl groups may be selected from phenyl groups, naphthyl groups, biphenyl groups, terphenyl groups, anthracenyl groups, fluorenyl groups, and carbazolyl groups substituted with at least one substituent selected from $C_1$-$C_5$ alkyl groups, $C_1$-$C_5$ alkoxy groups, cyano groups, amine groups, phenoxy groups, phenyl groups and halogen groups. The substituted $C_{12}$-$C_{50}$ arylamine groups may be selected from groups substituted with at least one substituent selected from $C_1$-$C_5$ alkyl groups, $C_1$-$C_5$ alkoxy groups, cyano groups, amine groups, phenoxy groups, phenyl groups and halogen groups.

Each of $R_2$ and $R_3$ may be independently selected from methyl groups and phenyl groups.

Each of $R_5$ and $R_{10}$ may be independently selected from t-butyl groups, phenyl groups, naphthyl groups, and fluorenyl groups.

Hereinafter, substituents described with reference to Formula 1 will now be described in detail.

The unsubstituted $C_1$-$C_{50}$ alkyl group may be linear or branched. Nonlimiting examples of the alkyl group include methyl groups, ethyl groups, propyl groups, isobutyl groups, sec-butyl groups, pentyl groups, iso-amyl groups, hexyl groups, heptyl groups, octyl groups, nonanyl groups, and dodecyl groups. At least one hydrogen atom of the alkyl group may be substituted with a substituent selected from heavy hydrogen atoms, halogen atoms, hydroxyl groups, nitro groups, cyano groups, amino groups, amidino groups, hydrazines, hydrazones, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups.

The unsubstituted $C_3$-$C_{50}$ cycloalkyl group refers to a $C_3$-$C_{50}$ cycloalkyl group. At least one hydrogen atom in the cycloalkyl group may be substituted with a substituent such as those described above with respect to the unsubstituted $C_1$-$C_{50}$ alkyl group.

The unsubstituted $C_1$-$C_{50}$ alkoxy group is a group having a structure of —OA wherein A is an unsubstituted $C_1$-$C_{50}$ alkyl group as described above. Nonlimiting examples of the alkoxy group include methoxy groups, ethoxy groups, propoxy groups, isopropyloxy groups, butoxy groups, and pentoxy groups. At least one hydrogen atom of the alkoxy group may be substituted with a substituent such as those described above with respect to the unsubstituted $C_1$-$C_{50}$ alkyl group.

The unsubstituted $C_6$-$C_{60}$ aryl group refers to a $C_6$-$C_{60}$ carbocyclic aromatic system containing at least one ring. When the $C_6$-$C_{60}$ carbocyclic aromatic system contains at least two rings, they may be fused to each other or linked to each other by a single bond. The term 'aryl' refers to an aromatic system, such as phenyl, naphthyl, or anthracenyl. In the aryl, one or more hydrogen atoms may be substituted with a substituent such as those described above with respect to the unsubstituted $C_1$-$C_{50}$ alkyl group.

Nonlimiting examples of the substituted or unsubstituted $C_6$-$C_{30}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ alkyl biphenyl groups, $C_1$-$C_{10}$ alkoxybiphenyl groups, o-, m-, and p-tolyl groups, o-, m-, and p-cumenyl groups, mesityl groups, phenoxyphenyl groups, ($\alpha,\alpha$-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_4$-$C_{60}$ heteroaryl group includes one, two or three hetero atoms selected from N, O, P and S. When the $C_4$-$C_{60}$ heteroaryl group contains at least two rings, they may be fused to each other or linked to each other by a single bond. Nonlimiting examples of the unsubstituted $C_4$-$C_{60}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. In the heteroaryl group, one or more hydrogen atoms may be substituted with a substituent such as those described above with respect to the unsubstituted $C_1$-$C_{50}$ alkyl group.

The unsubstituted $C_5$-$C_{50}$ aryloxy group is represented by —OA$_1$ where A$_1$ may be a $C_5$-$C_{60}$ aryl group. Nonlimiting examples of the aryloxy group include phenoxy groups. In the aryloxy group, one or more hydrogen atom may be substituted with a substituent such as those described above with respect to the unsubstituted $C_1$-$C_{50}$ alkyl group.

The unsubstituted $C_5$-$C_{50}$ arylthio group is represented by —SA$_1$ where A$_1$ may be a $C_5$-$C_{60}$ aryl group. Nonlimiting examples of the arylthio group include phenylthio groups, naphthylthio groups, and fluorenylthio groups. In the arylthio group, one or more hydrogen atoms may be substituted with a substituent such as those described above with respect to the unsubstituted $C_1$-$C_{50}$ alkyl group.

The unsubstituted $C_6$-$C_{60}$ condensed polycyclic group refers to a substituent including at least two rings wherein at least one aromatic ring and/or at least one non-aromatic ring are fused to each other. The unsubstituted $C_6$-$C_{60}$ condensed polycyclic group may be substituted with at least one substituent such as those described above with respect to the aryl group or the heteroaryl group.
Nonlimiting examples of the heterocyclic compound of Formula 1 according to embodiments of the present invention include Compounds 1 through 95 represented below.
1
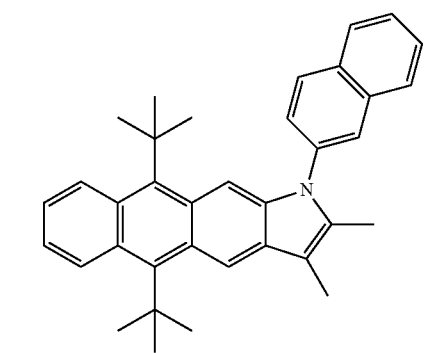
2
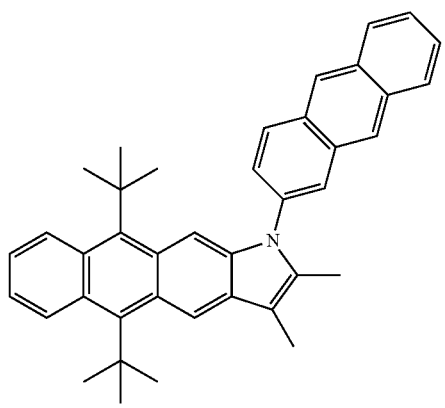
3
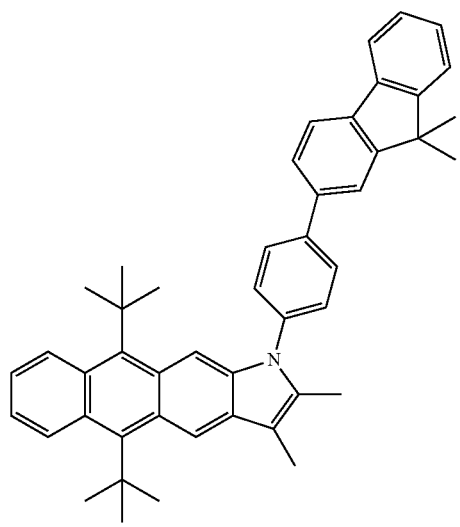
-continued
4
5
6
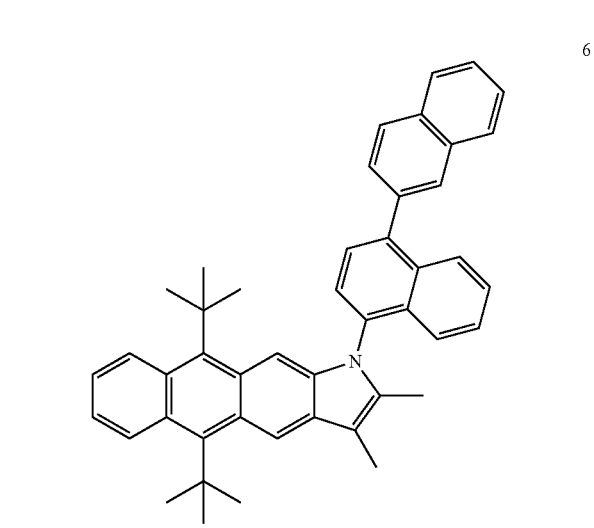

-continued
7
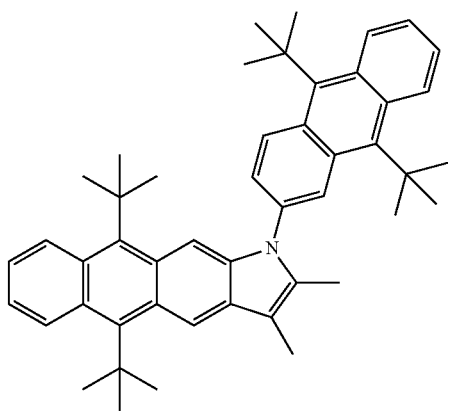
8
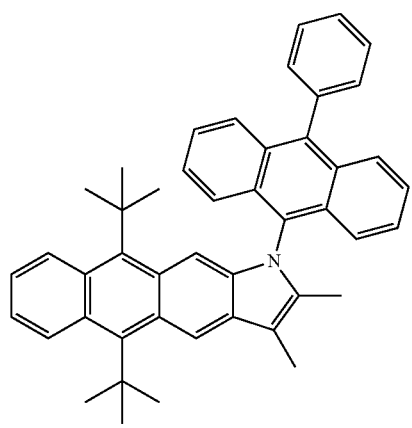
9
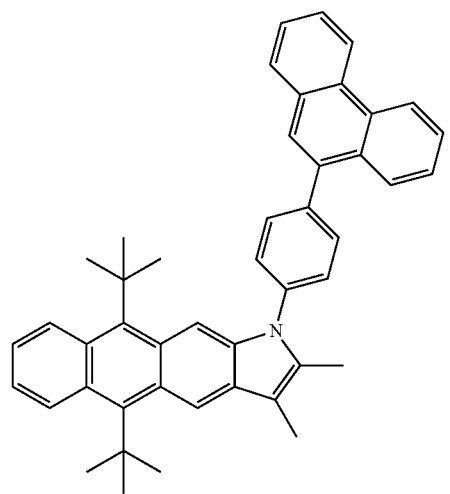
-continued
10
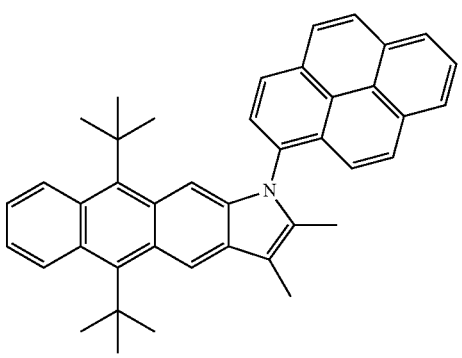
11
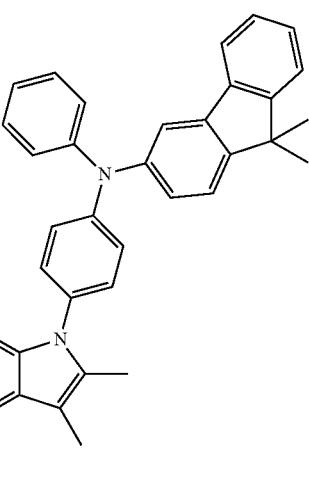
12
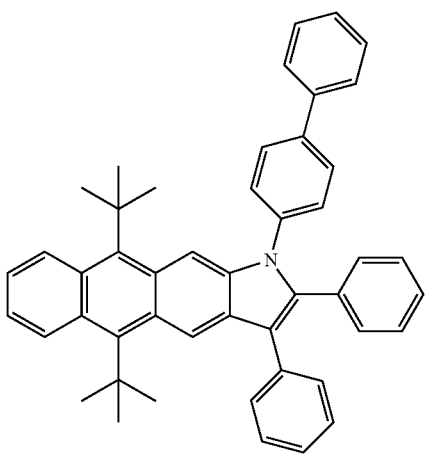

13
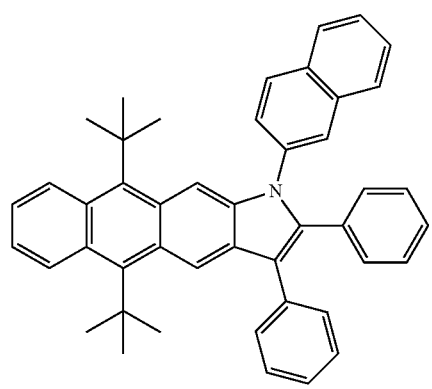
14
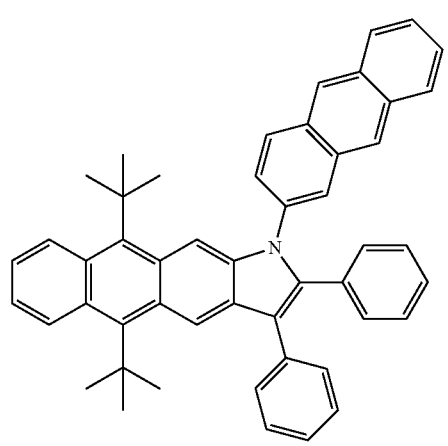
15
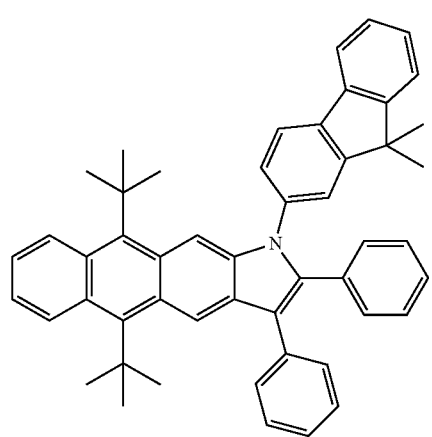
16
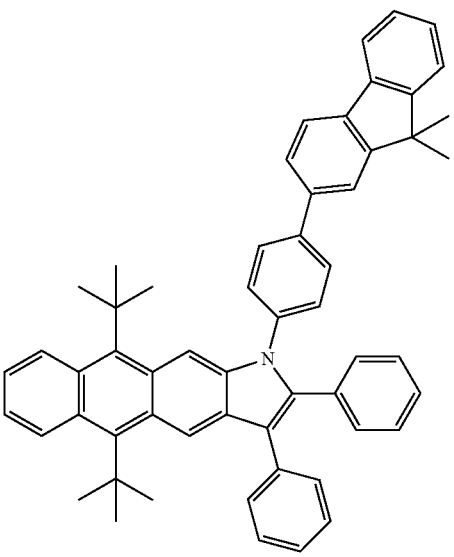
17
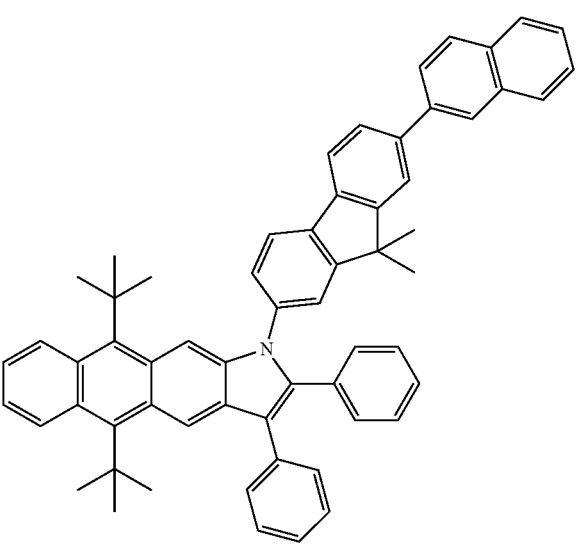

18
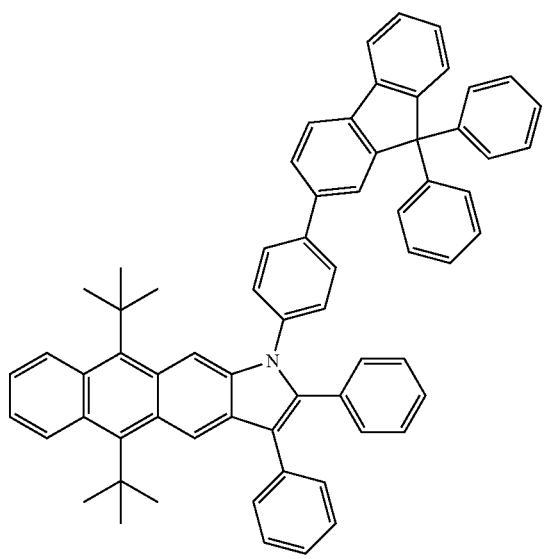
19
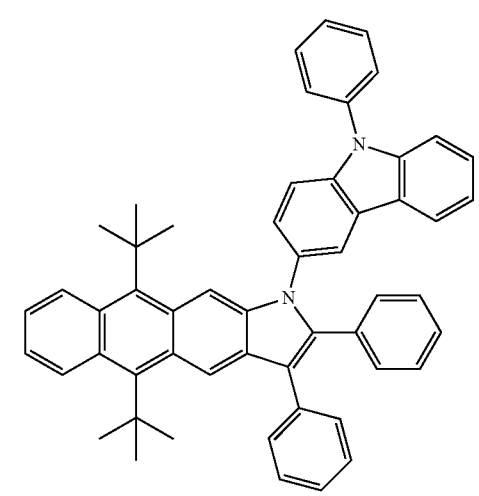
20
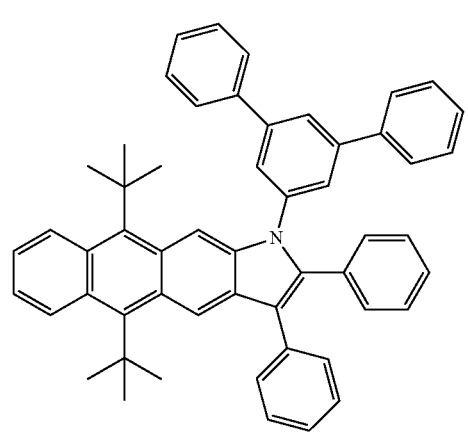
21
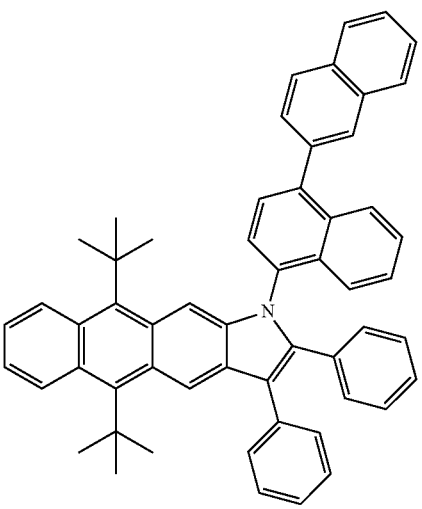
22
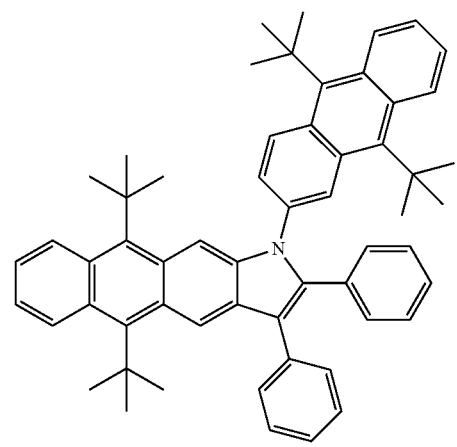
23
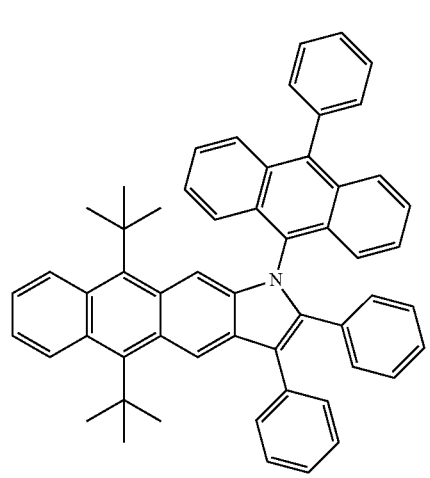

24
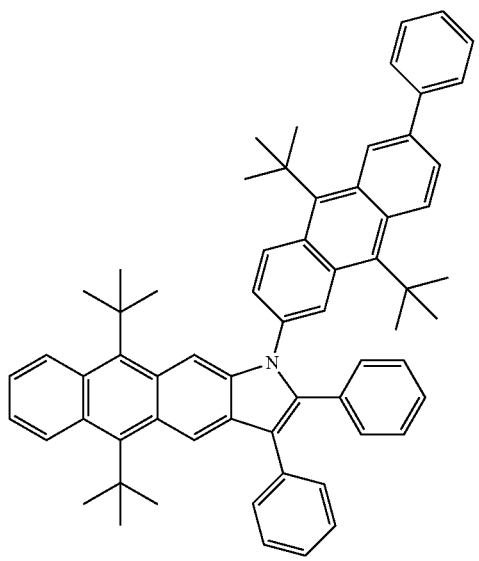
25
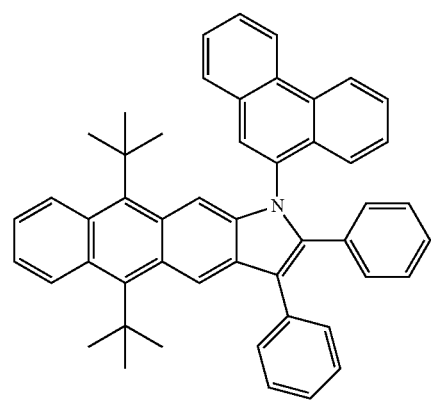
26
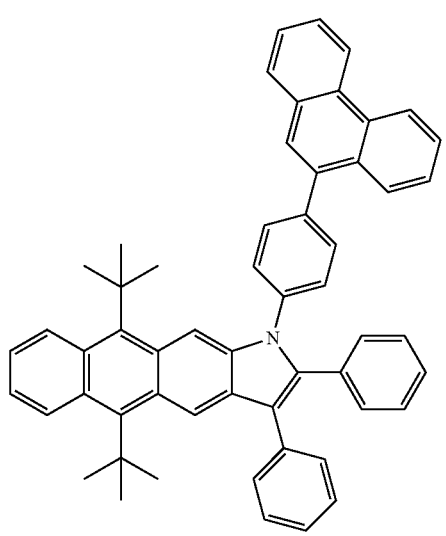
27
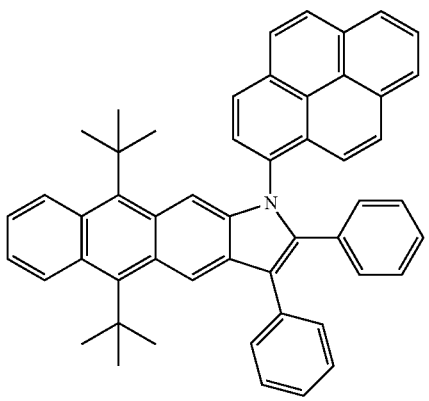
28
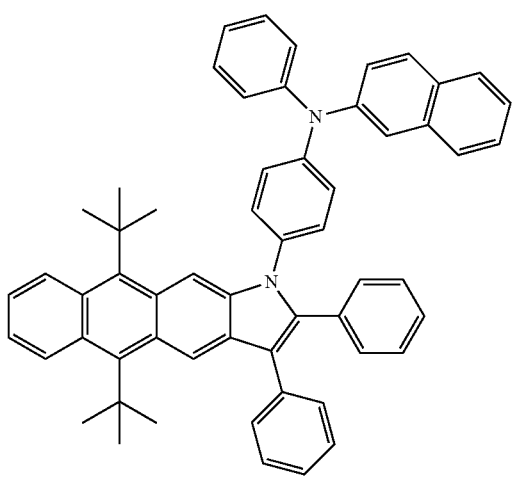
29
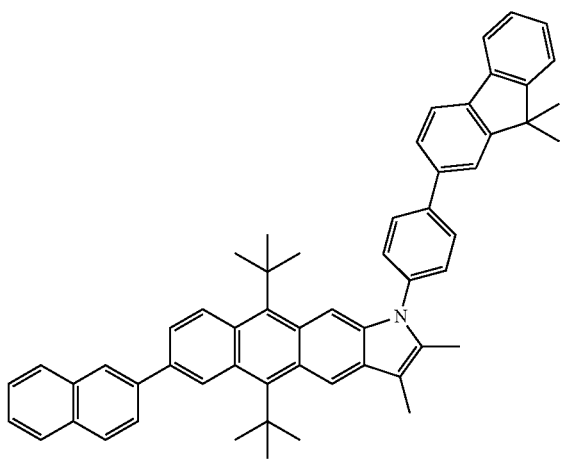

30
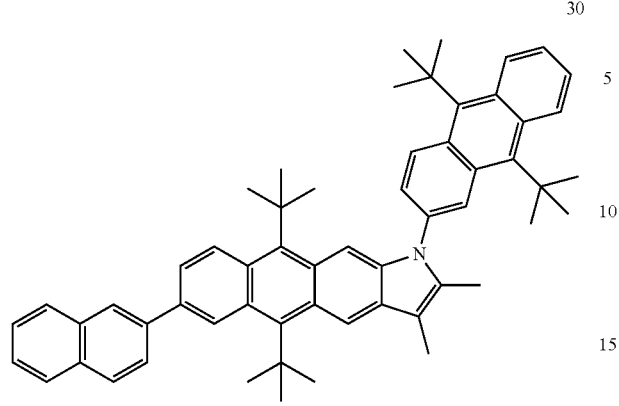
31
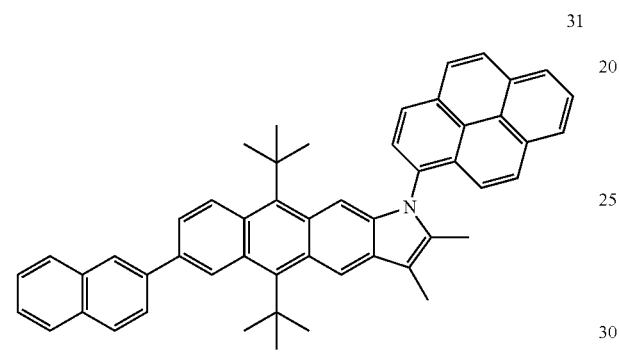
32
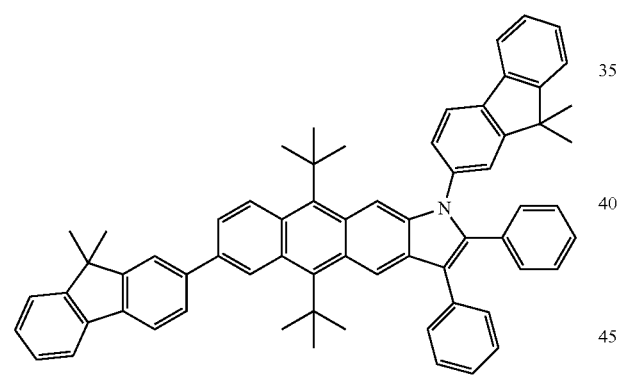
33
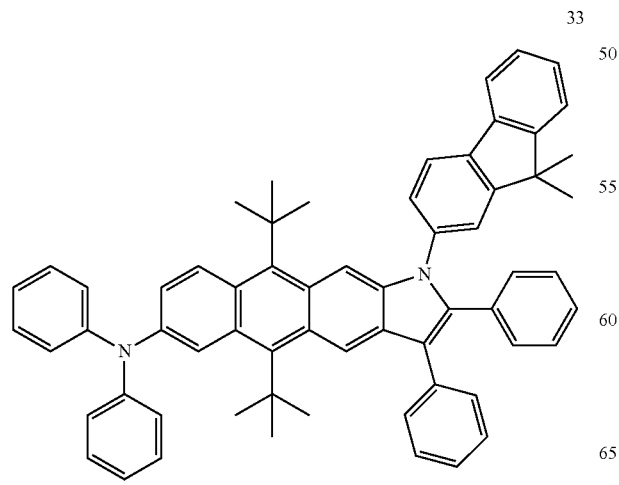
34
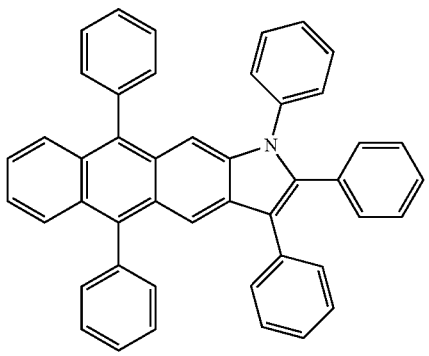
35
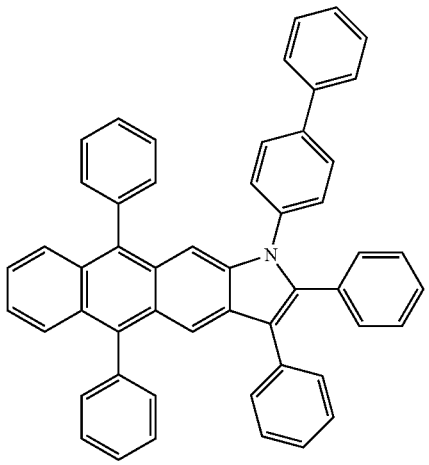
36
37
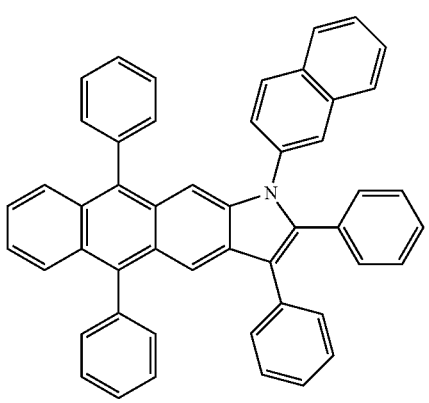

38
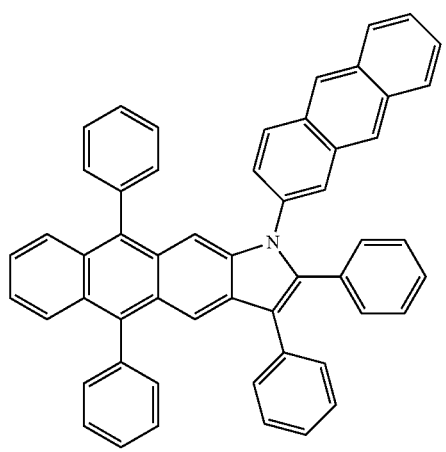
39
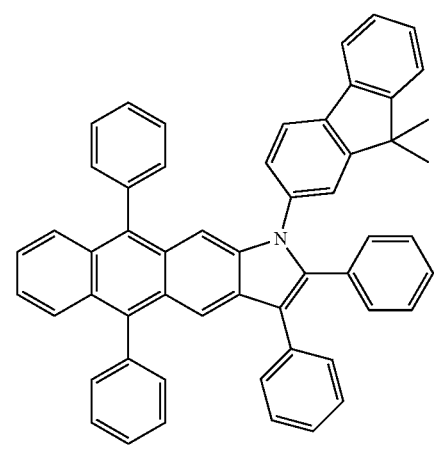
40
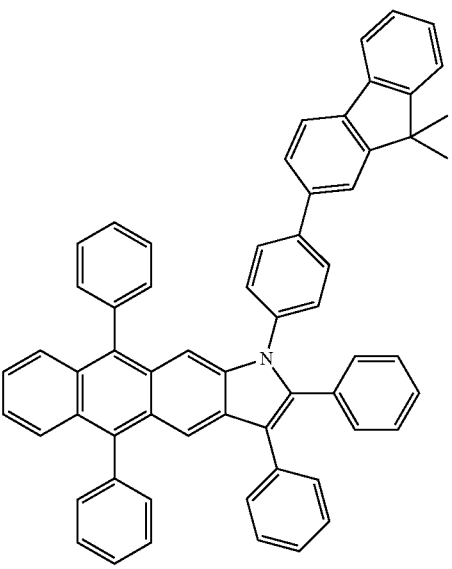
41
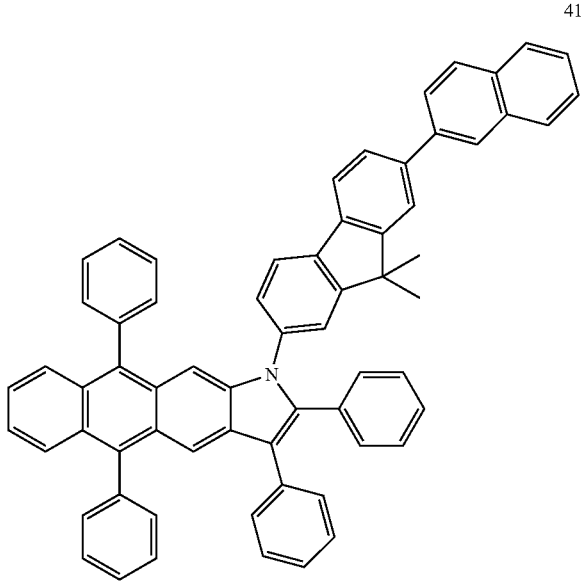
42
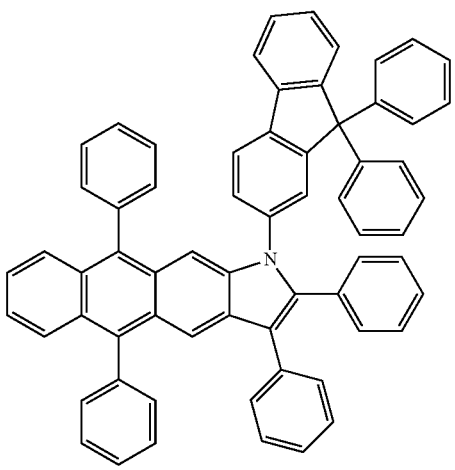
43
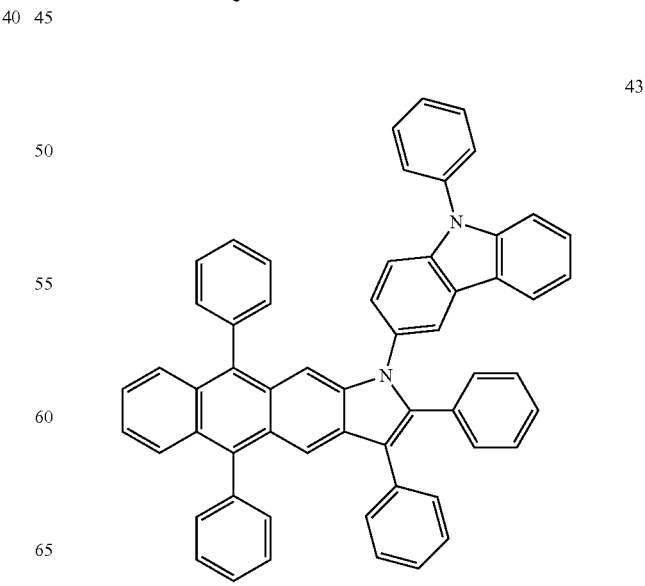

44
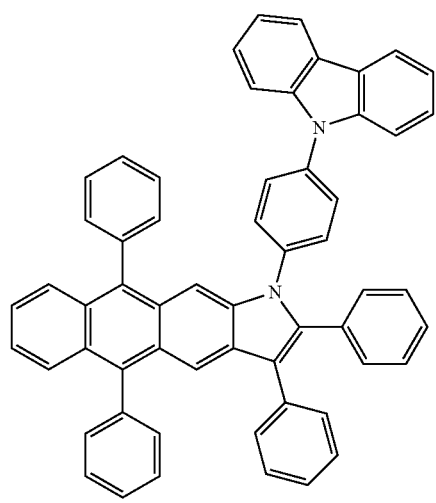
45
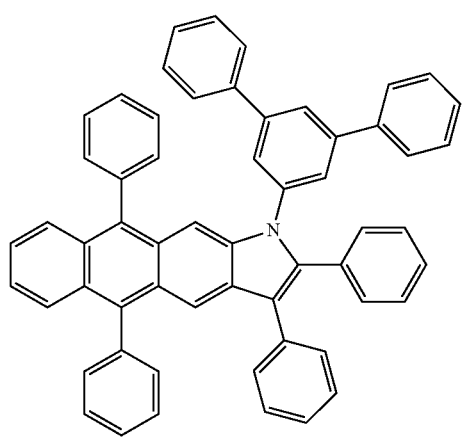
46
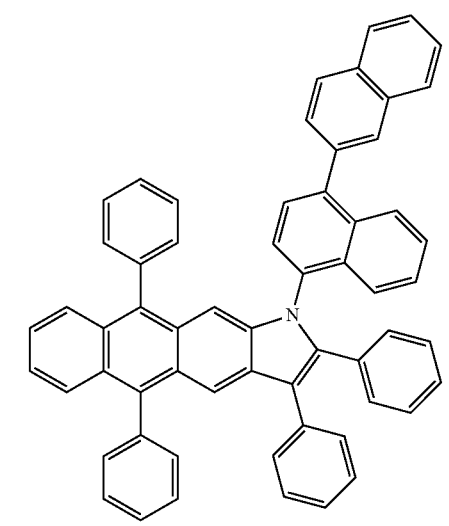
47
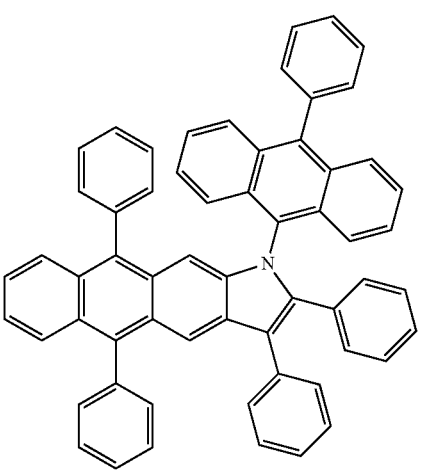
48
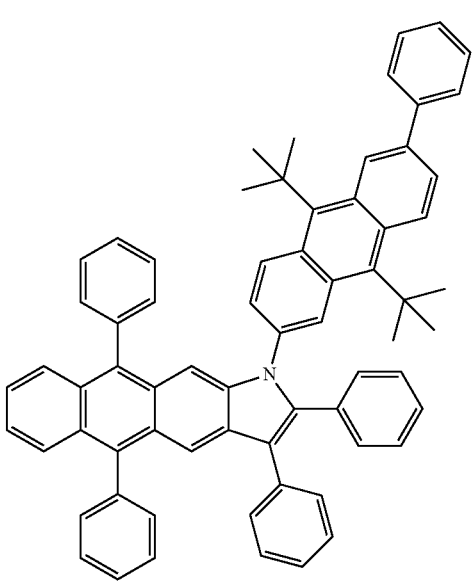
49
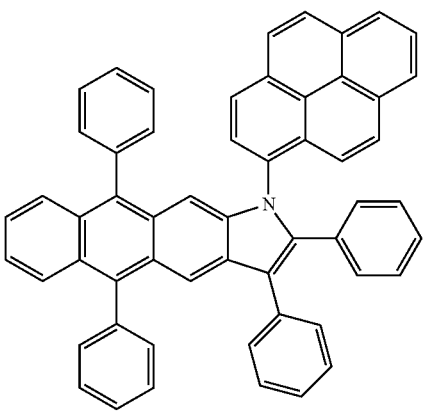

50
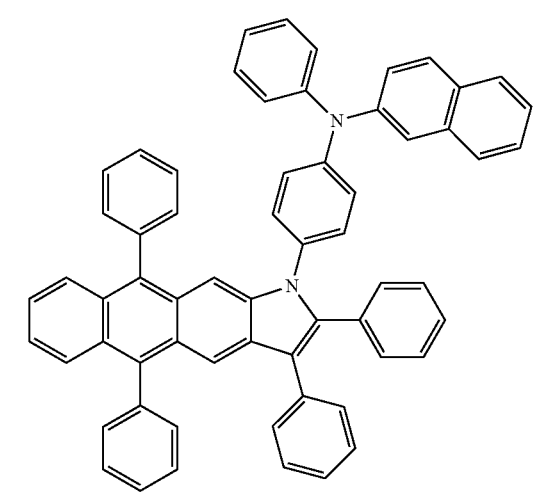
51
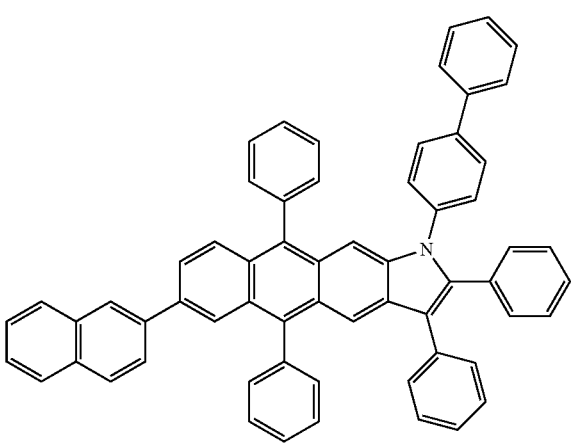
52
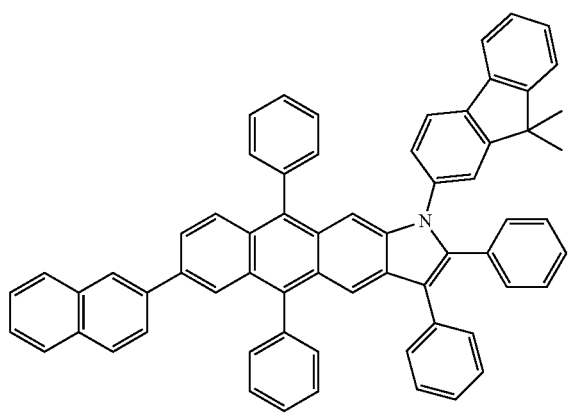
53
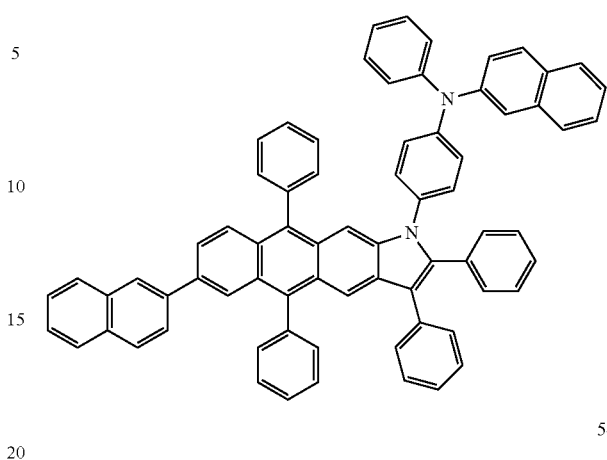
54
55
56
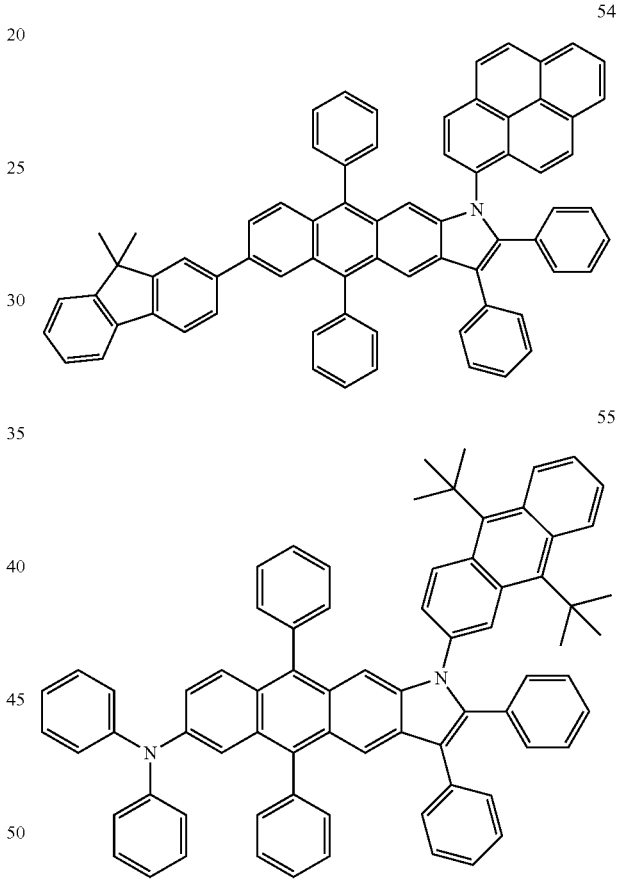

57
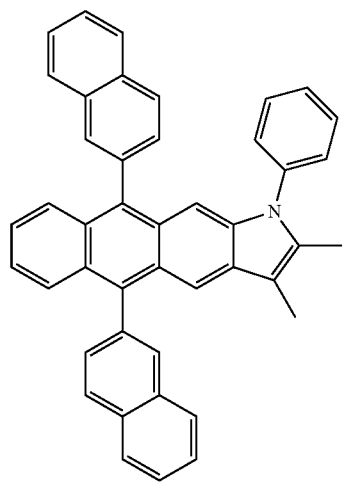
58
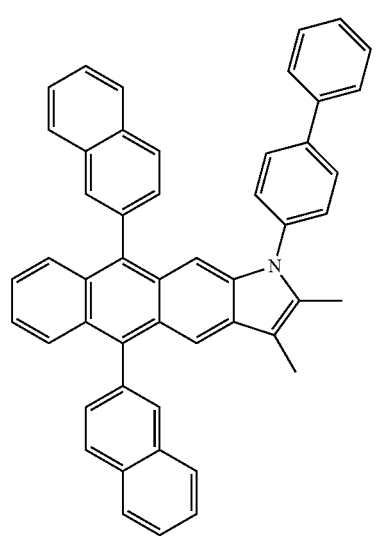
59
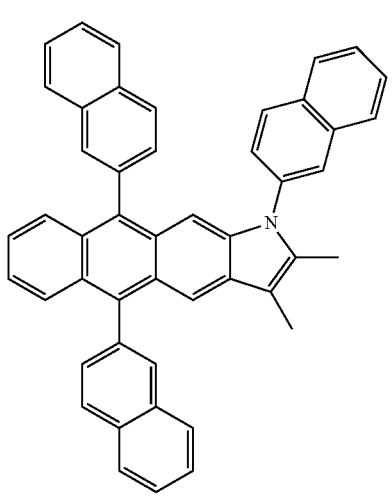
60
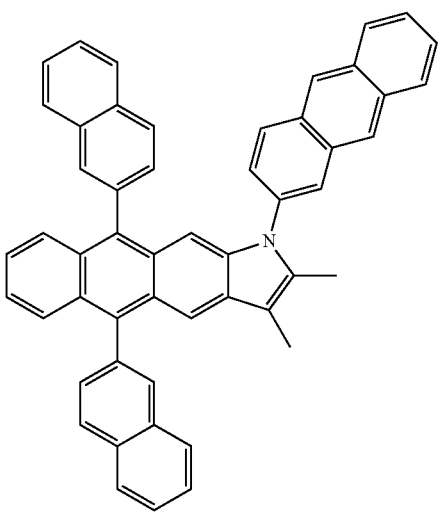
61
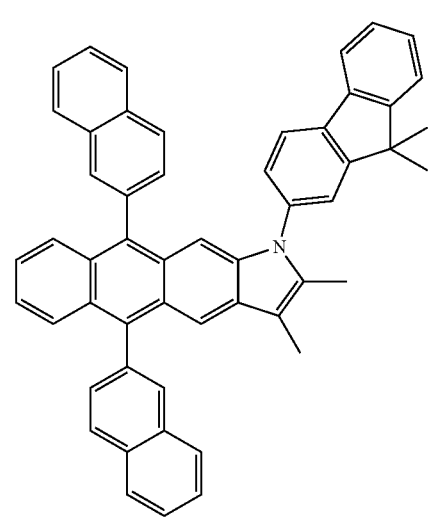
62
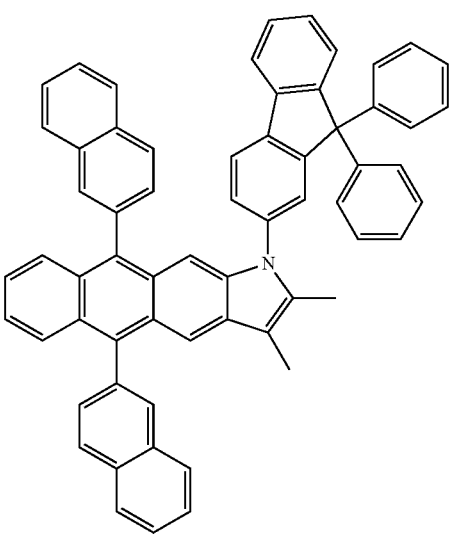

-continued
63
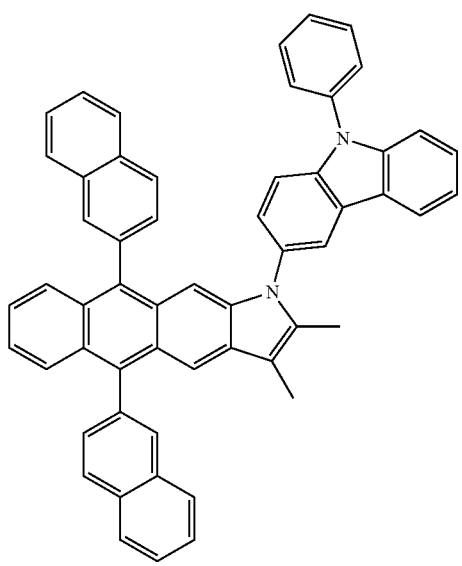
64
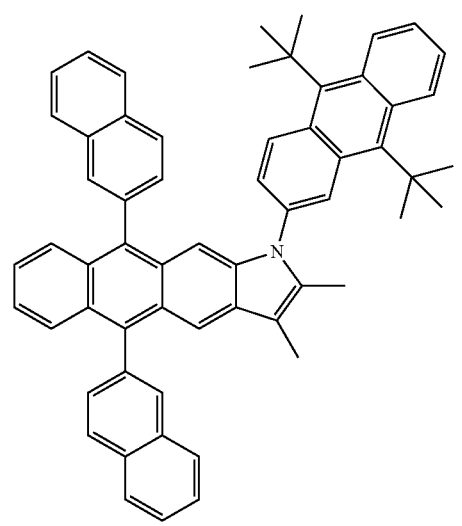
65
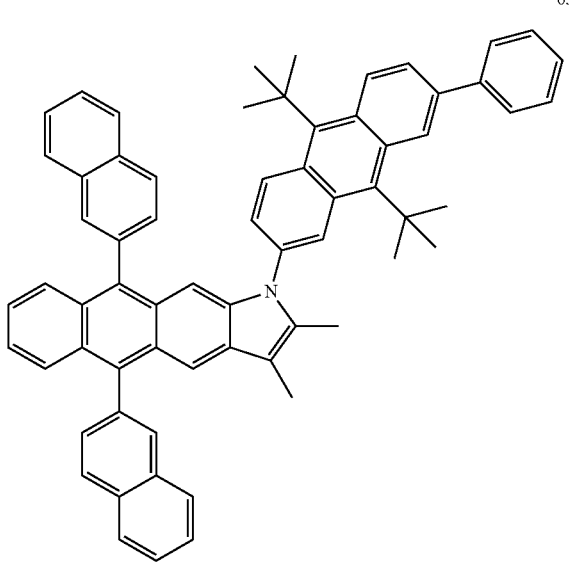
-continued
66
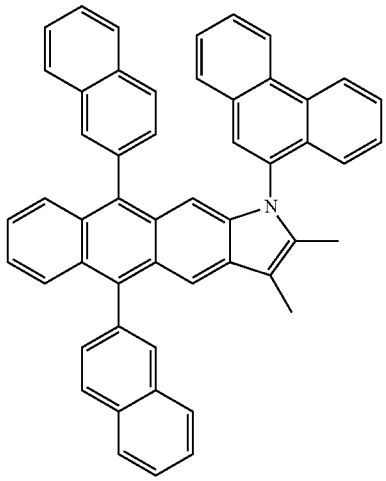
67
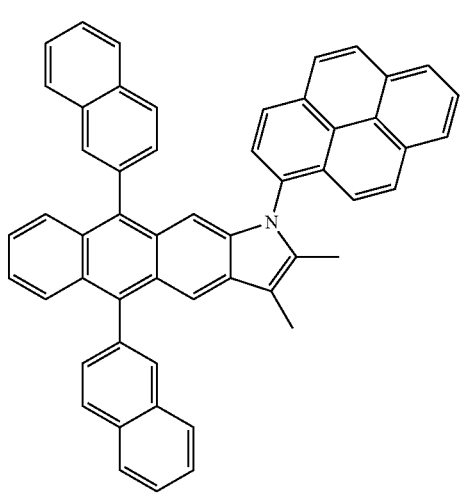
68
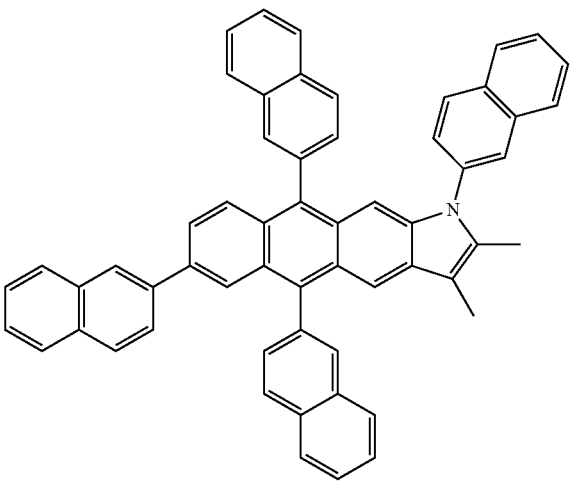

-continued
69
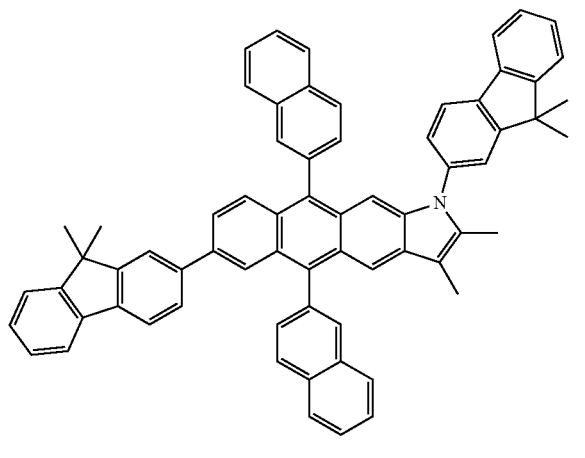
70
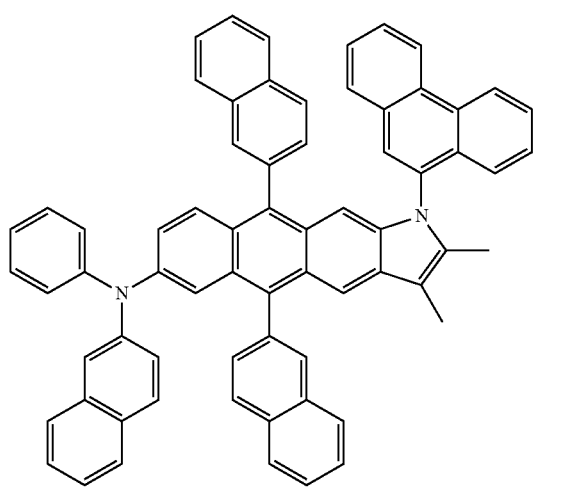
71
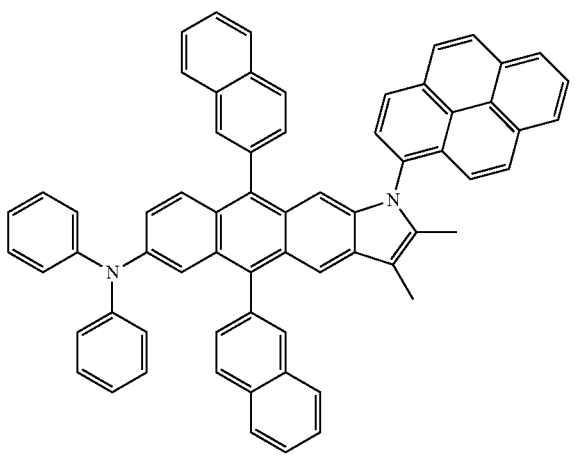
-continued
72
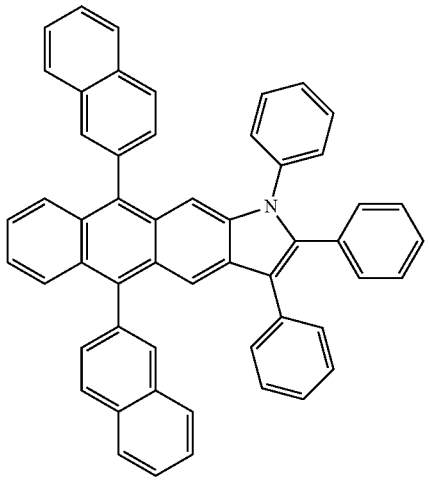
73
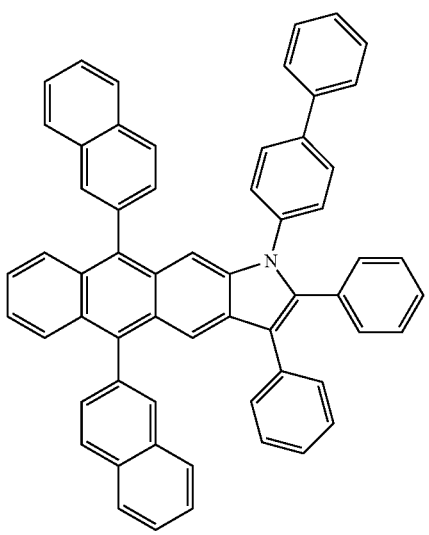
74
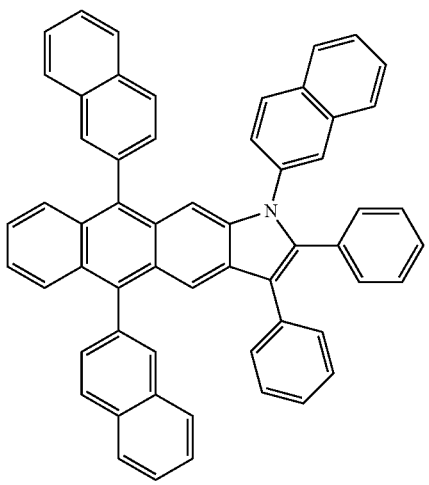

75
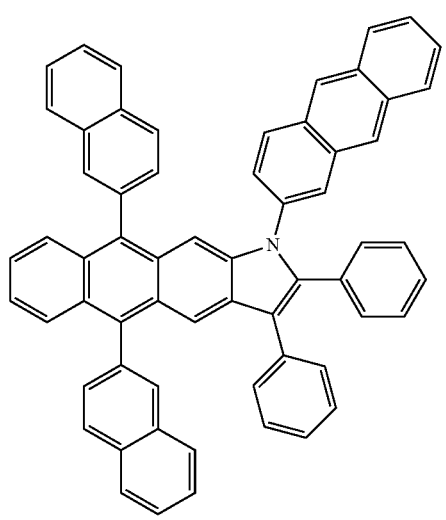
76
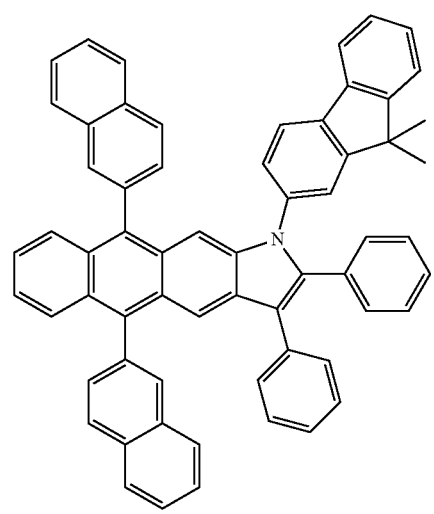
77
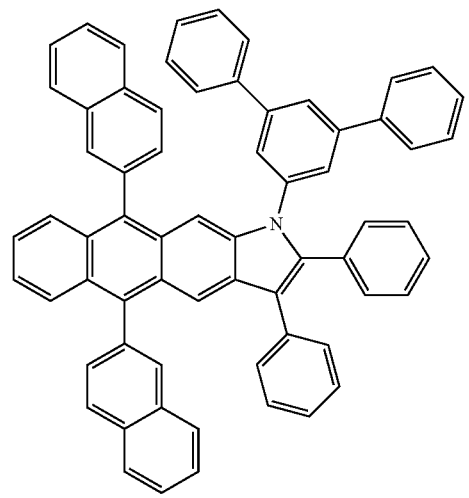
78
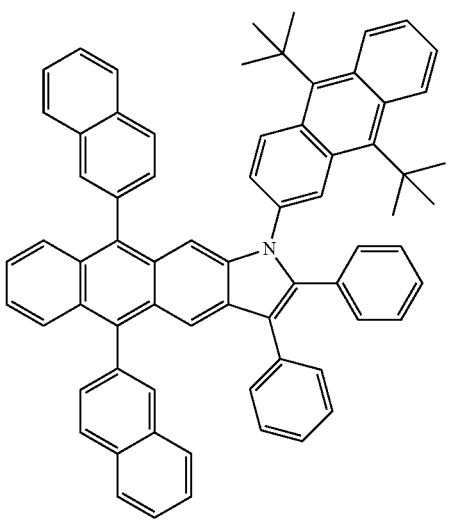
79
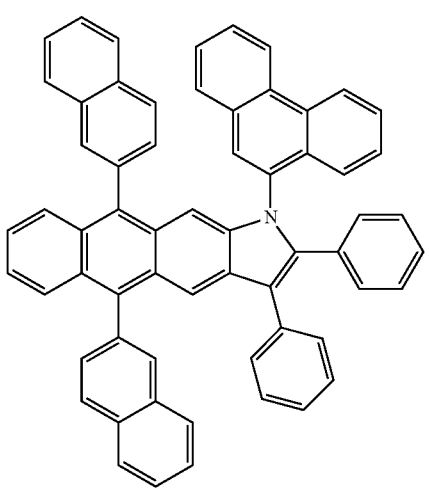
80
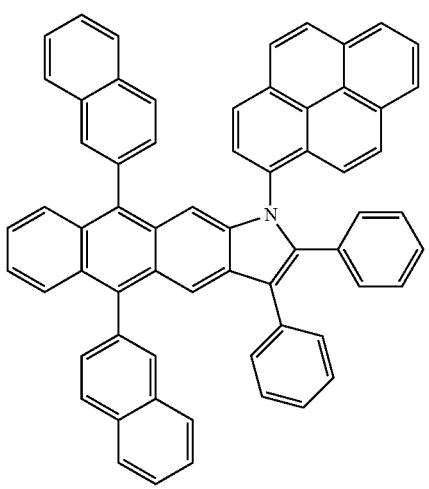

81
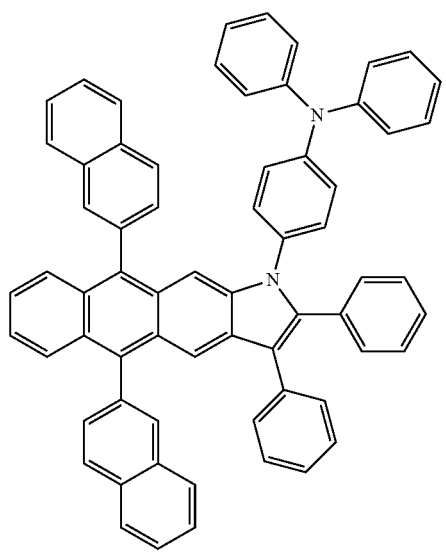
82
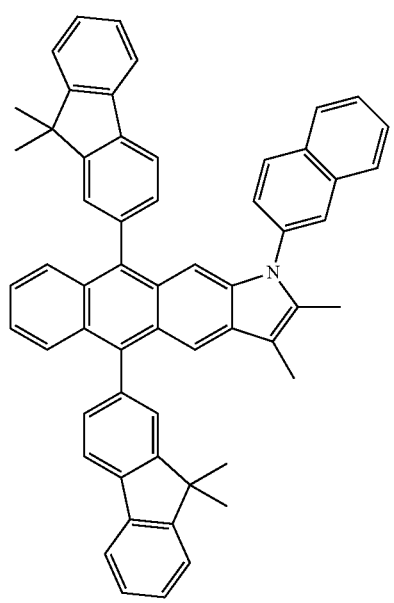
83
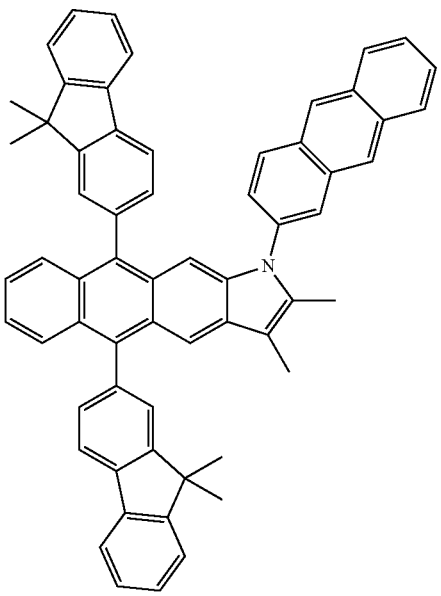
84
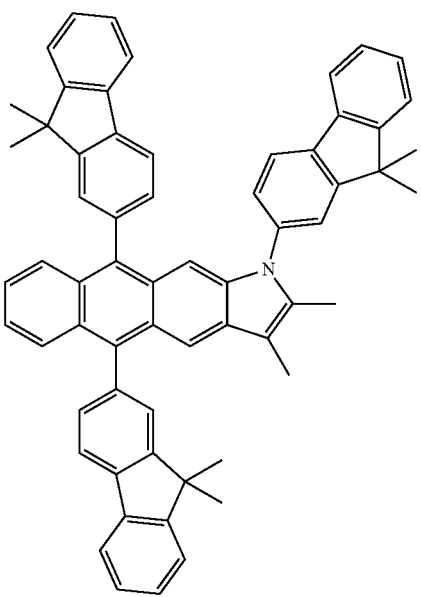

85
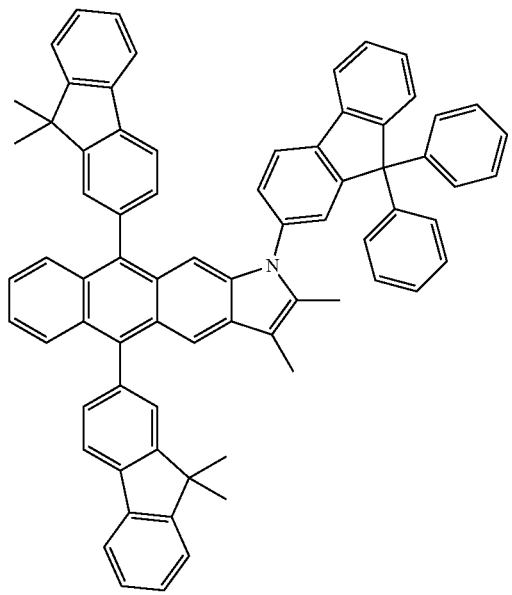
86
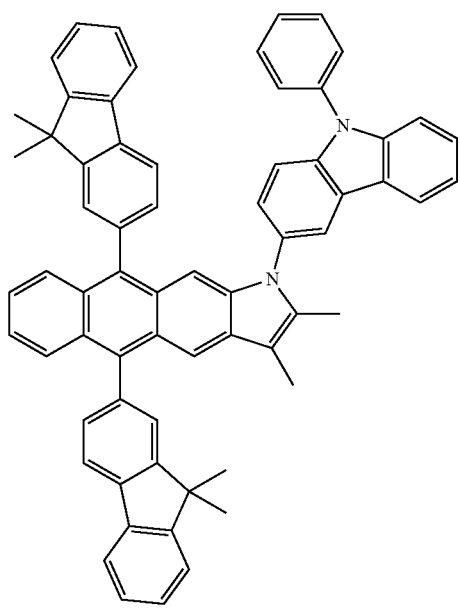
87
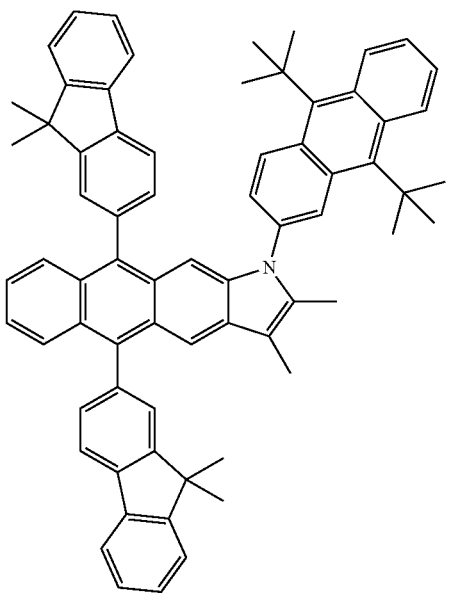
88
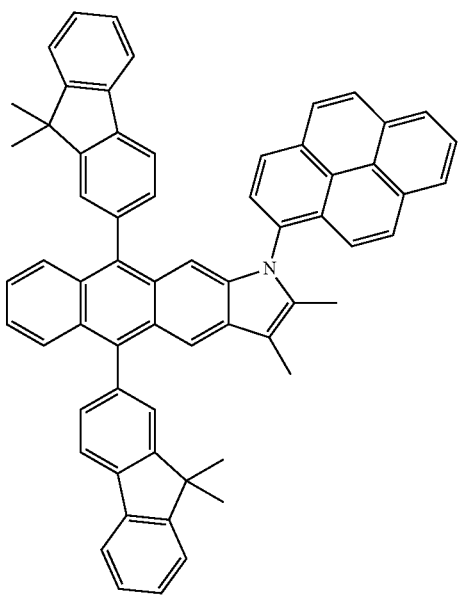

39
-continued
89
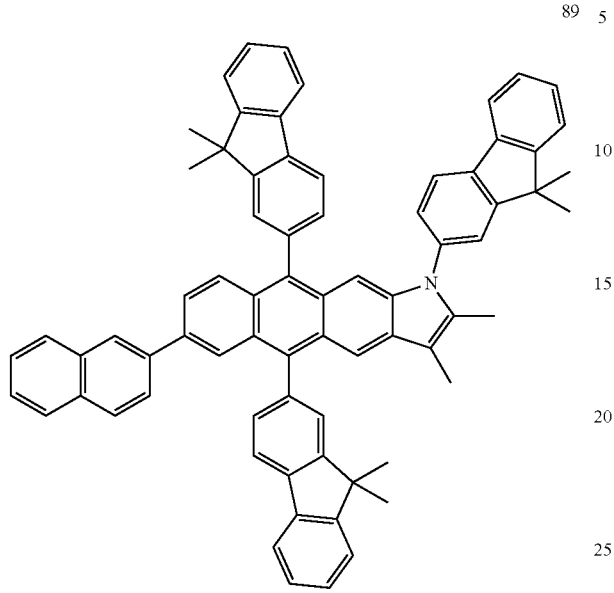
40
-continued
91
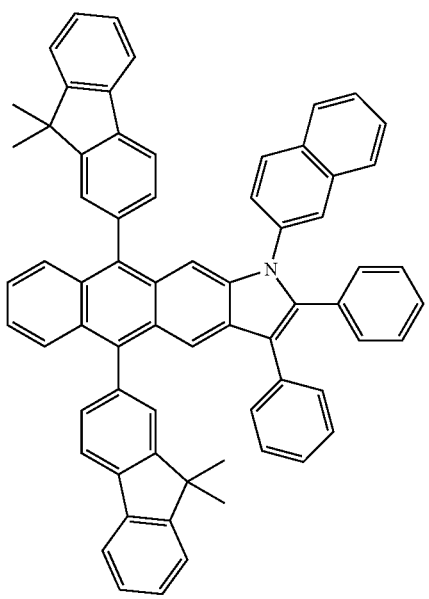
90
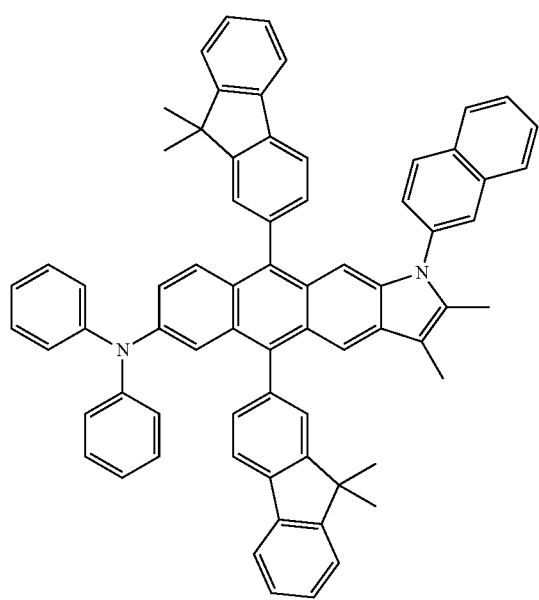
92
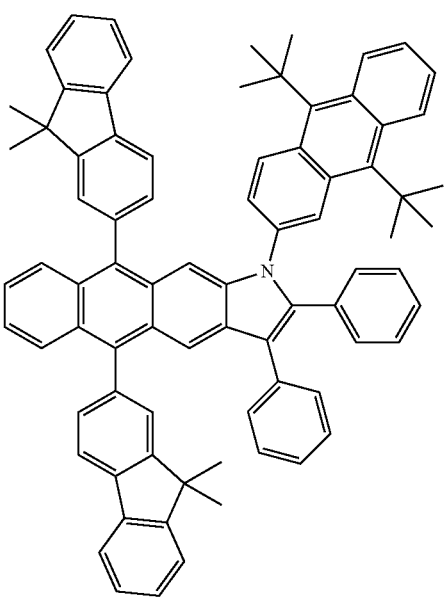

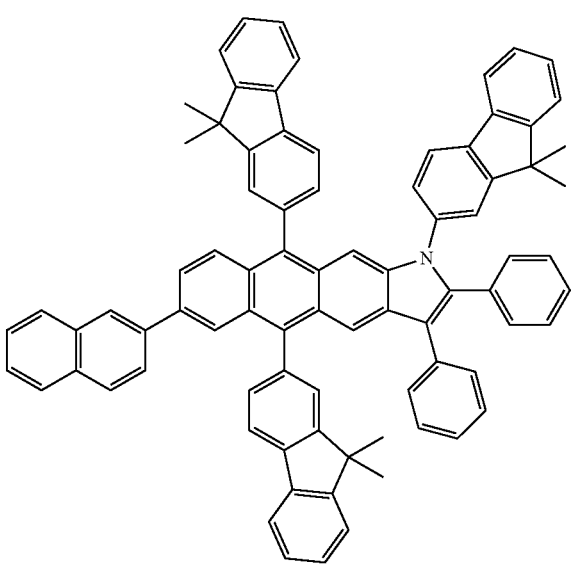

93

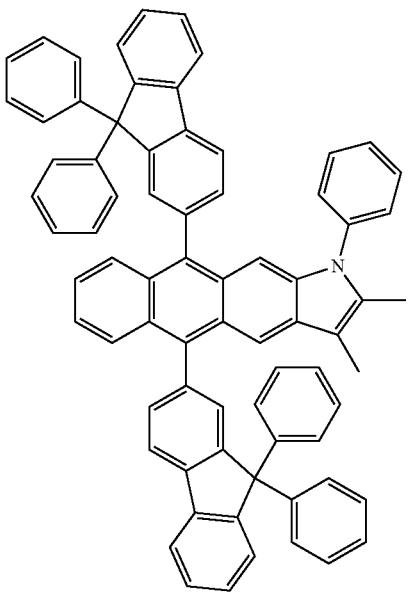

95

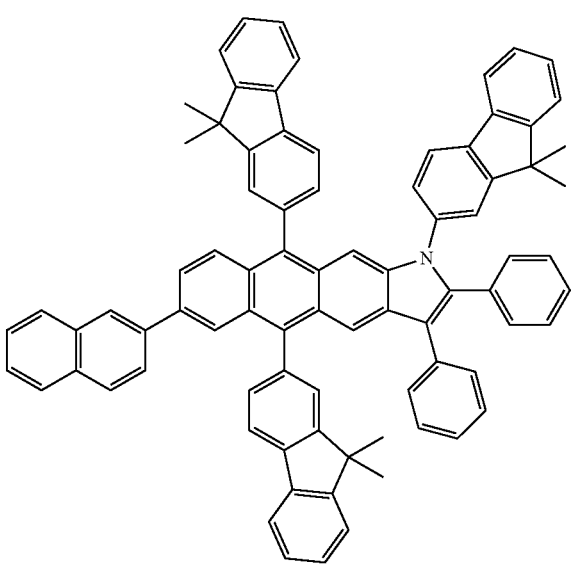

94

An organic light-emitting device according to an embodiment of the present invention includes a first electrode, a second electrode, and an organic layer between the first electrode and the second electrode, wherein the organic layer includes the heterocylic compound of Formula 1 described above.

The organic layer including the heterocyclic compound of Formula 1 may be an electron injection layer (EIL), an electron transport layer (ETL), or a single layer having both electron injection and electron transport capabilities. Alternatively, the organic layer including the heterocyclic compound of Formula 1 may be an EML. When the organic layer including the heterocyclic compound of Formula 1 is an EML, the heterocyclic compound of Formula 1 may be used as a fluorescent host, a phosphorescent host, or a fluorescent dopant.

In the organic light-emitting device according to embodiments of the present invention, when the EML, the EIL or the ETL includes the heterocyclic compound of Formula 1, the EML may include an anthracene compound, an arylamine compound or a styryl compound. The anthracene compound, the arylamine compound or the styryl compound may be unsubstituted or substituted with a substituent such as those described above with respect to the unsubstituted $C_1$-$C_{50}$ alkyl group.

In the organic light-emitting device according to embodiments of the present invention, when the EIL, ETL or EML includes the heterocyclic compound of Formula 1, a red EML, a green EML, a blue EML or a white EML may include a phosphorescent compound.

The first electrode may be an anode, and the second electrode may be a cathode, but the reverse is also possible.

In the organic light-emitting device described above, the organic layer may further include at least one layer selected from a HIL, a HTL, an electron blocking layer (EBL), an EML, a hole blocking layer (HBL), an ETL and an EIL, if desired. For example, the organic light-emitting device according to embodiments of the present invention may have a first electrode/HIL/EML/second electrode structure, a first electrode/HIL/HTL/EML/ETL/second electrode structure, or a first electrode/HIL/HTL/EML/ETL/EIL/second electrode structure. Alternatively, the organic light-emitting device may have a first electrode/single layer having both hole injection and hole transport capabilities/EML/ETL/second electrode structure, or a first electrode/single layer having both hole injection and hole transport capabilities/EML/ETL/EIL/second electrode structure.

The organic light emitting device according to embodiments of the present invention may be a top-emission type organic light-emitting device or a bottom-emission type organic light-emitting device.

Hereinafter, a method of manufacturing an organic light-emitting device according to an embodiment of the present invention will be described with reference to FIG. 1. FIG. 1 illustrates the structure of an organic light-emitting device according to an embodiment of the present invention. Referring to FIG. 1, the organic light-emitting device includes a substrate, a first electrode (anode), a HIL, a HTL, an EML, an ETL, an EIL, and a second electrode (cathode).

First, a first electrode is formed on a substrate by deposition or sputtering. The first electrode may be formed of a first electrode material having a high work function. The first electrode may be an anode or a cathode. The substrate may be any substrate commonly used in organic light-emitting devices, and may be, for example, a glass substrate or a transparent plastic substrate having good mechanical strength, thermal stability, transparency, surface planarity, handling convenience, and water resistance. The first electrode material may include at least one material selected from indium tin oxide (ITO), indium zinc oxide (IZO), tin oxide ($SnO_2$), zinc oxide (ZnO), aluminum (Al), silver (Ag), and magnesium (Mg), which have good conductivity, and may form a transparent or reflective electrode.

Next, a HIL may be formed on the first electrode by various methods, for example, vacuum deposition, spin coating, casting, Langmuir-Blodgett (LB) method, or the like. When the HIL is formed using vacuum deposition, the deposition conditions may vary according to the compound used to form the HIL, and the desired structural and thermal characteristics of the HIL to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, the coating conditions may vary according to the compound used to form the HIL, and the structural and thermal properties of the HIL to be formed. For example, the coating conditions may include a coating speed of about 2000 rpm to about 5000 rpm, and a thermal treatment temperature of about 80° C. to about 200° C., wherein the thermal treatment removes the solvent after the coating.

The HIL material may include the heterocyclic compound of Formula 1 described above. Alternatively, known HIL materials may also be used. Nonlimiting examples of HIL materials include phthalocyanine compounds such as copper phthalocyanine, 4,4',4"-tris(3-methylphenylphenylamino)triphenylamine (m-MTDATA), N,N'-di(1-naphthyl)-N,N'-diphenylbenzidine) (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and (polyaniline)/poly(4-styrenesulfonate) (PANI/PSS).

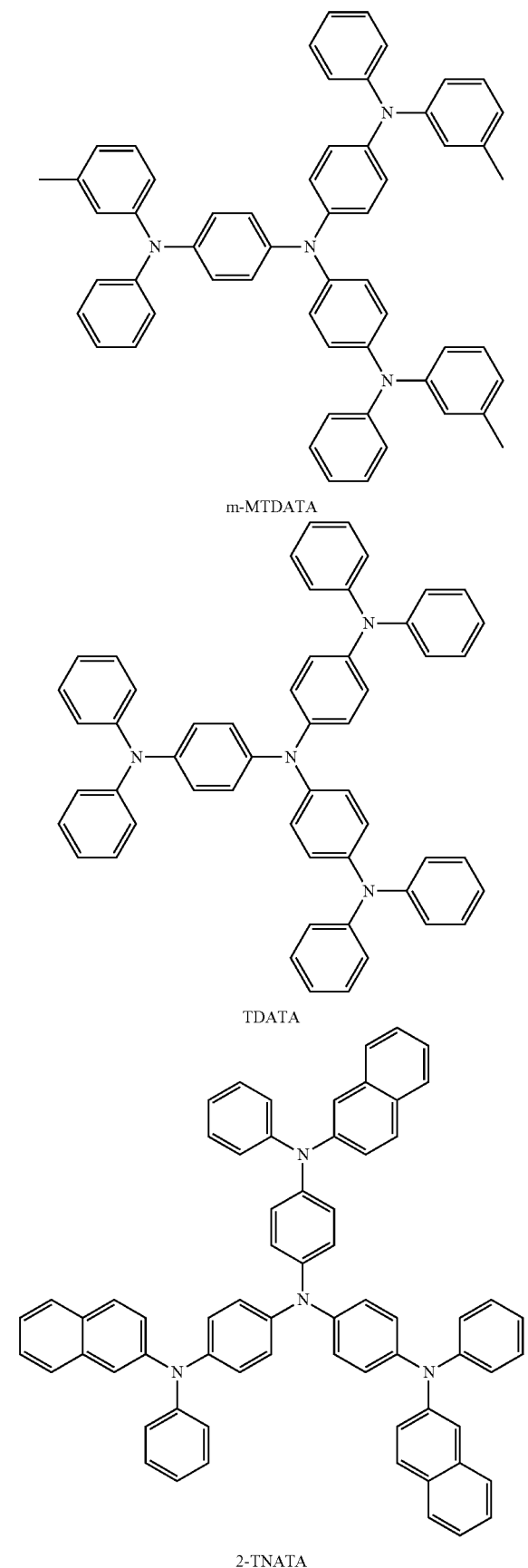

m-MTDATA

TDATA

2-TNATA

The HIL may have a thickness of about 100 Å to about 10000 Å. In some embodiments, for example, the HIL has a thickness of about 100 Å to about 1000 Å. When the HIL has a thickness within these ranges, the HIL has good hole injection characteristics without increasing driving voltage.

Then, a HTL may be formed on the HIL by vacuum deposition, spin coating, casting, LB method, or the like. When the HTL is formed using vacuum deposition or spin coating, the deposition or coating conditions may be similar to those used to form the HIL, although the deposition or coating conditions may vary according to the material that is used to form the HTL.

The HTL material may include the heterocyclic compound of Formula 1 described above. Alternatively, known HTL materials may be used. Nonlimiting examples of HTL materials include carbazole derivatives such as N-phenylcarbazole and polyvinylcarbazole, and amine derivatives having an aromatic condensed ring, such as NPB, or N,N'-bis(3-methylphenyl)-N,N'-diphenyl-[1,1-biphenyl]-4,4'-diamine (TPD). Among these materials, TCTA not only transports holes but also inhibits excitons from being diffused from the EML.

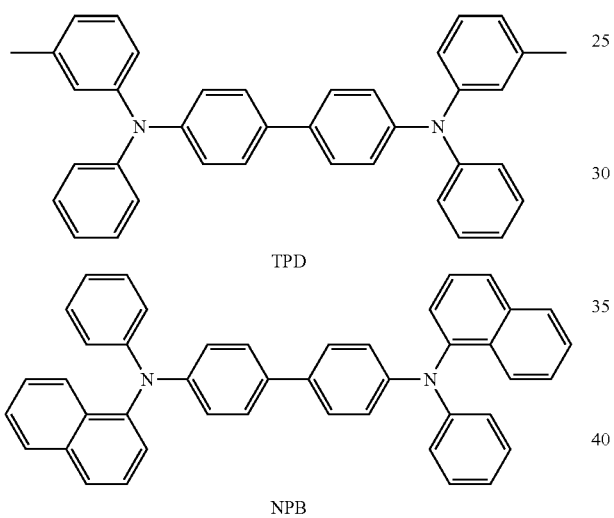

TPD

NPB

The HTL may have a thickness of about 50 Å to about 1000 Å. In some embodiments, for example, the HTL has a thickness of 100 Å to about 600 Å. When the HTL has a thickness within these ranges, the HTL has good hole transport characteristics without substantially increasing driving voltage.

Then, an EML may be formed on the HTL by vacuum deposition, spin coating, casting, LB method, or the like. When the EML is formed using vacuum deposition or spin coating, the deposition or coating conditions may be similar to those used to form the HIL, although the deposition and coating conditions may vary according to the material that is used to form the EML.

The EML may include the heterocyclic compound of Formula 1 described above. In particular, the heterocyclic compound of Formula 1 may be used as a host or a dopant. The EML may include a variety of known light-emitting materials, in addition to the heterocyclic compound of Formula 1. Alternatively, the EML may also include a known host and dopant. The dopant used to form the EML may include either a fluorescent dopant or a phosphorescent dopant.

Nonlimiting examples of the host include $Alq_3$, 4,4'-N,N'-dicarbazole-biphenyl (CPB), 9,10-di(naphthalene-2-yl)anthracene (ADN), and distyrylarylene (DSA).

Nonlimiting examples of red dopants include platinum(II) octaethylporphyrin (PtOEP), $Ir(piq)_3$, $Btp_2Ir(acac)$, and DCJTB.

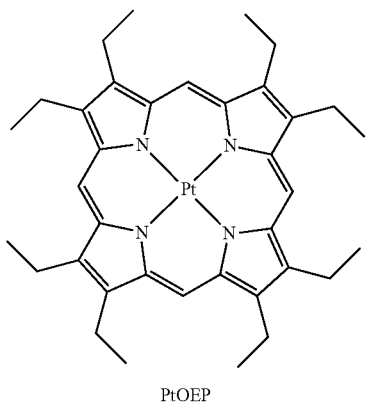

PtOEP

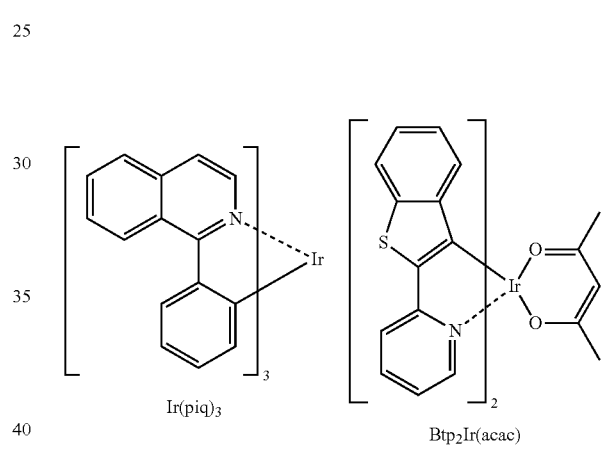

$Ir(piq)_3$ $Btp_2Ir(acac)$

Nonlimiting examples of green dopants include $Ir(ppy)_3$, where "ppy" denotes phenylpyridine, $Ir(ppy)_2(acac)$, $Ir(m-pyp)_3$, and C545T.

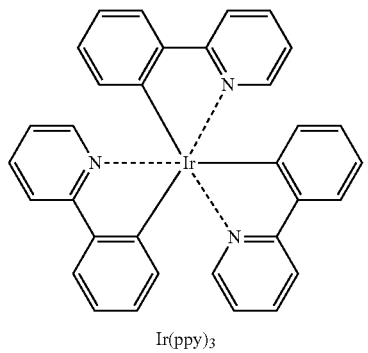

$Ir(ppy)_3$

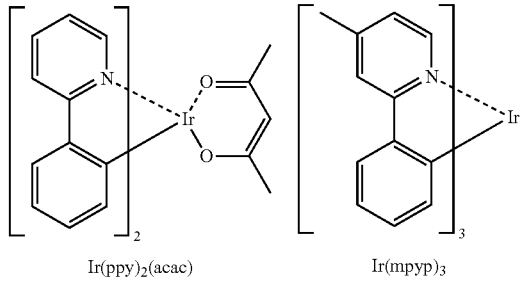
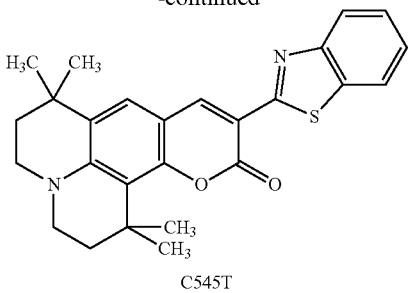
Nonlimiting examples of blue dopants include $F_2$Irpic, $(F_2ppy)_2$Ir(tmd), Ir(dfppz)$_3$, ter-fluorene, 4,4'-bis(4-diphenylaminostyryl)biphenyl (DPAVBi), and 2,5,8,11-tetra-t-butyl pherylene (TBPe).
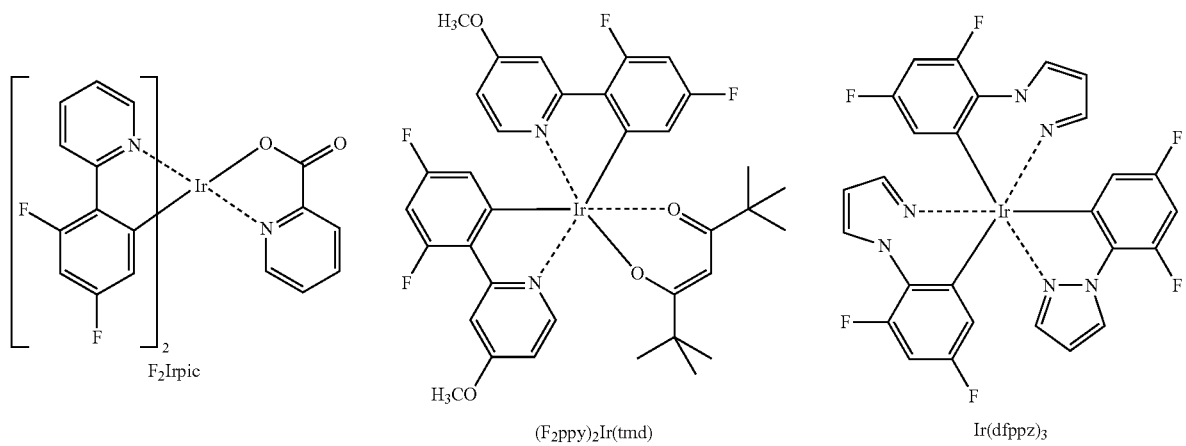
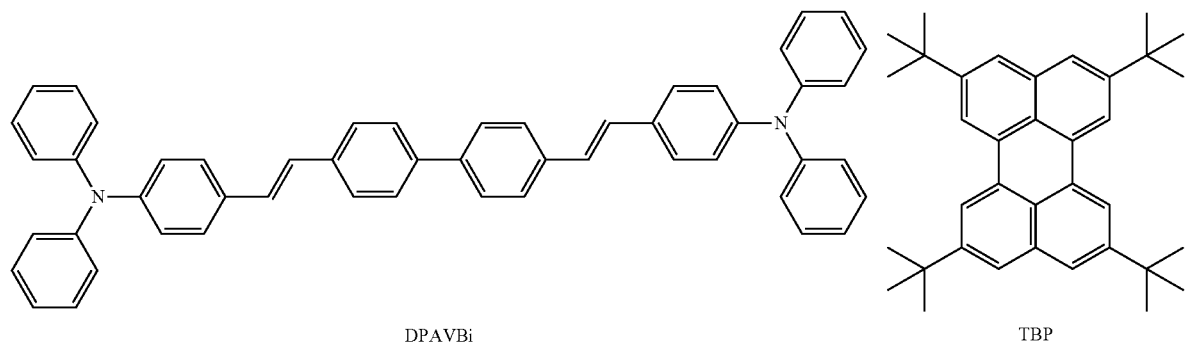

The amount of the dopant may be about 0.1 to about 20 parts by weight based on 100 parts by weight of the EML material (i.e., the total weight of the host and the dopant). In some embodiments, the amount of the dopant may be about 0.5 to about 12 parts by weight based on 100 parts by weight of the EML material. When the content of the dopant is within these ranges, concentration quenching may be substantially prevented.

The EML may have a thickness of about 100 Å to about 1000 Å. In some embodiments, for example, the EML has a thickness of about 200 Å to about 600 Å. When the EML has a thickness within these ranges, the EML has good light-emitting characteristics without substantially increasing driving voltage.

When the EML includes a phosphorescent dopant, a HBL (not shown in FIG. 1) may be formed on the EML to prevent diffusion of triplet excitons or holes into the ETL. The HBL may be formed of any material commonly used to form a HBL, without limitation. Nonlimiting examples of HBL materials include oxadiazole derivatives, triazole derivatives, phenanthroline derivatives, Balq, and BCP.

The HBL may have a thickness of about 50 Å to about 1000 Å. In some embodiments, for example, the HBL has a thickness of about 100 Å to about 300 Å. When the thickness of the HBL is within these ranges, the HBL may have good hole blocking capability without substantially increasing driving voltage.

Then, an ETL may be formed on the HBL or EML by vacuum deposition, spin coating, casting, or the like. When the ETL is formed using vacuum deposition or spin coating, the deposition or coating conditions may be similar to those used to form the HIL, although the deposition and coating conditions may vary according to the material that is used to form the ETL.

The ETL material may include the heterocyclic compound of Formula 1 described above. Alternatively, the ETL may be formed of any material known in the art. Nonlimiting examples of ETL materials include quinoline derivatives, such as tris(8-quinolinolate)aluminum ($Alq_3$), TAZ, or Balq.

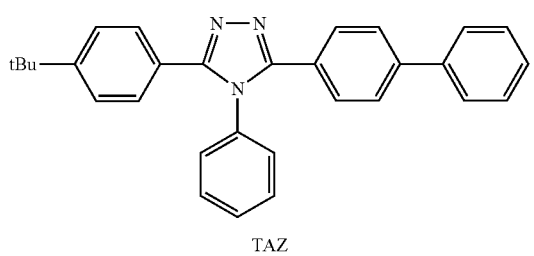

TAZ

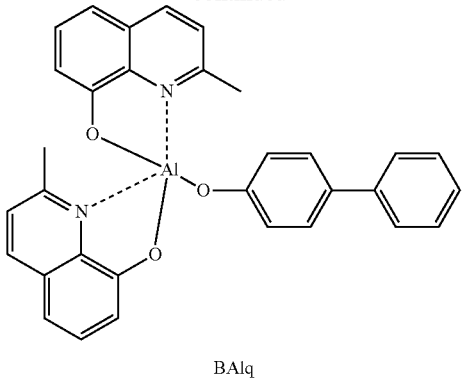

BAlq

The ETL may have a thickness of about 100 Å to about 1000 Å. In some embodiments, for example, the ETL has a thickness of about 100 Å to about 500 Å. When the ETL has a thickness within these ranges, the ETL may have good electron transport characteristics without substantially increasing driving voltage.

In addition, an EIL, which facilitates injection of electrons from the cathode, may be formed on the ETL.

The EIL material may include the heterocyclic compound of Formula 1 described above. Alternatively, known EIL materials, such as LiF, NaCl, CsF, $Li_2O$, or BaO, may be used to form the EIL. The deposition or coating conditions may be similar to those used to form the HIL, although the deposition and coating conditions may vary according to the material that is used to form the EIL.

The EIL may have a thickness of about 1 Å to 100 Å. In some embodiments, for example, the EIL has a thickness of about 5 Å to about 90 Å. When the EIL has a thickness within these ranges, the EIL may have good electron injection characteristics without substantially increasing driving voltage.

Finally, a second electrode may be formed on the EIL by, for example, vacuum deposition, sputtering, or the like. The second electrode may be a cathode or an anode. The material for forming the second electrode may be a metal, an alloy, or an electrically conductive compound with a low work function. Nonlimiting examples of second electrode materials include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission type organic light-emitting device, a transparent cathode formed of a transparent material such as ITO or IZO may be used.

The organic light-emitting device according to embodiments of the present invention may be included in various types of flat panel display devices, such as passive matrix organic light-emitting display devices or active matrix organic light-emitting display devices. When the organic light-emitting device is included in an active matrix organic light-emitting display device including a thin-film transistor, the first electrode formed on the substrate may function as a pixel electrode, and is electrically connected to a source electrode or a drain electrode of the thin-film transistor. Moreover, the organic light-emitting device may also be included in flat panel display devices having double-sided screens.

According to embodiments of the present invention, at least one layer of the organic light-emitting device may be formed of the heterocyclic compound of Formula 1 and may be applied by a deposition method or a wet method of coating a solution of the heterocylic compound of Formula 1.

The following examples are presented for illustrative purposes only, an do not limit the scope of the present invention.

EXAMPLES

Synthesis Example

Synthesis of Compound 11

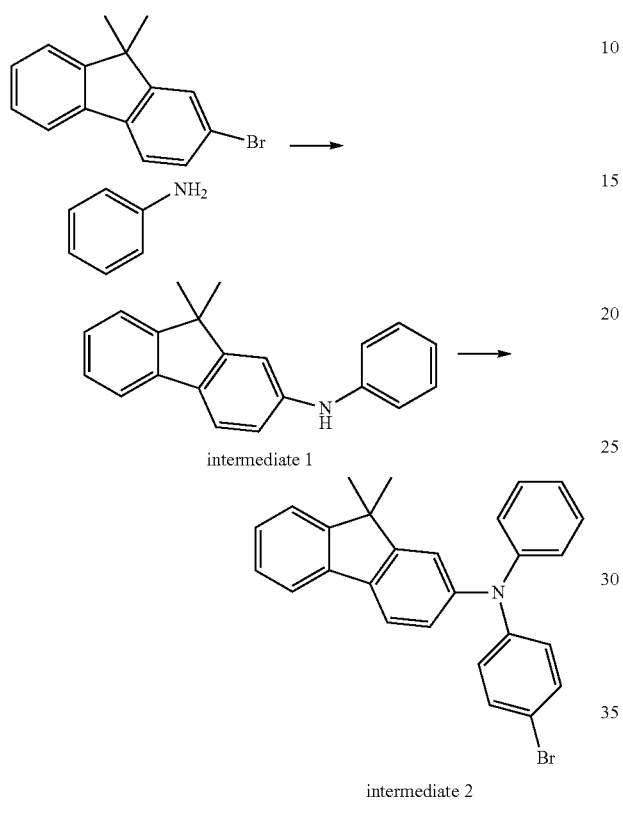

intermediate 1 intermediate 2

Synthesis of Intermediate 1

27.3 g (100.0 mmol) of 2-bromo-9,9-dimethylfluorene, 11.2 g (120.0 mmol) of aniline, 14.4 g (150.0 mmol) of NaOt-Bu, 4.5 g (5.0 mmol) of $Pd_2(dba)_3$, and 1.0 g (5.0 mmol) of Pt-$Bu_3$ were dissolved in 300 ml of toluene, and the mixture was maintained at 90° C. for 5 hours in a nitrogen atmosphere. The mixture was cooled to room temperature, and 100 mL of water was added thereto. Then, the mixture was subjected to extraction twice with 300 ml of methylene chloride. An organic layer was collected and dried, followed by filtration and concentration. The residue was separated by column chromatography to obtain 20.1 g (yield: 78%) of pale yellow Intermediate 1.

Synthesis of Intermediate 2

14.3 g (50.0 mmol) of Intermediate 1, 28.3 g (100.0 mmol) of 4-bromoiodobenzene, 7.2 g (75.0 mmol) of NaOt-Bu, 2.3 g (2.5 mmol) of $Pd_2(dba)_3$, and 0.5 g (2.5 mmol) of Pt-$Bu_3$ were dissolved in 150 mL of toluene, and the mixture was maintained at 90° C. for 5 hours in a nitrogen atmosphere. The mixture was cooled to room temperature, and 50 mL of water was added thereto. Then, the mixture was subjected to extraction twice with 200 ml of methylene chloride. An organic layer was collected and dried, followed by filtration and con- centration. The residue was separated by column chromatography to obtain 13.6 g (yield: 62%) of pale yellow Intermediate 2. The structure of this compound was identified using high-resolution mass spectra (HR-MS). (calc.; 439.0936, found; 439.0923)

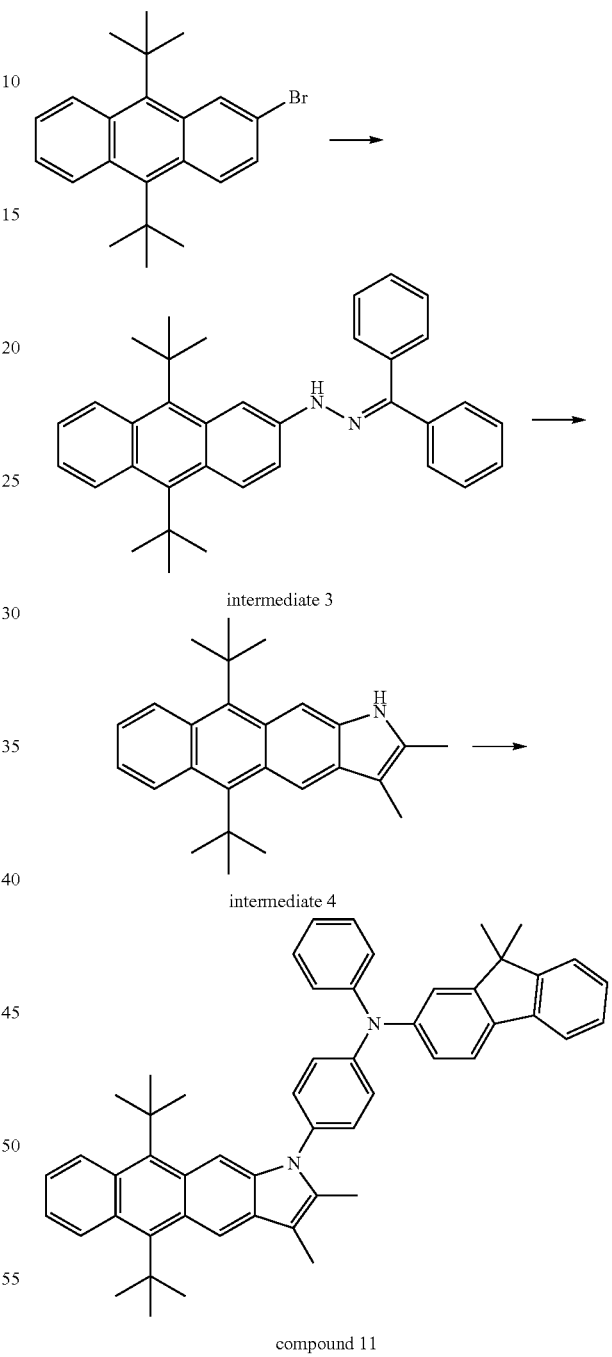

intermediate 3 intermediate 4 compound 11

Synthesis of Intermediate 3

37.0 g (100.0 mmol) of 2-bromo-9,9'-di-t-butylanthracene, 20.3 g (120 mmol) of benzophenone hydrazone, 14.4 g (150.0 mmol) of NaOt-Bu, 1.1 g (5.0 mmol) of $Pd(Oac)_2$, and 2.4 g (5.0 mmol) of 2-dicyclohexyl phosphino-2',4',6'-triisopropylbiphenyl were dissolved in 300 mL of toluene, and the mixture was maintained at 90° C. for 3 hours in a nitrogen atmosphere. The mixture was cooled to room temperature, and 100 mL of water was added thereto. Then, the mixture was subjected to extraction twice with 300 ml of methylene chloride. An organic layer was collected and dried, followed by filtration and concentration. The residue was separated by column chromatography to obtain 39.7 g (yield: 82%) of yellowish green solid Intermediate 3.

Synthesis of Intermediate 4

38.8 g (80.0 mmol) of Intermediate 3 and 30.4 g (160.0 mmol) of p-toluene sulfonic acid were dissolved in 300 mL of methyl ethyl ketone, and the mixture was maintained at 80° C. for 12 hours in a nitrogen atmosphere. The mixture was cooled to room temperature, the solvent was concentrated under a reduced pressure, and 100 mL of water was added thereto. Then, the mixture was subjected to extraction twice with 200 ml of methylene chloride. An organic layer was collected and dried, followed by filtration and concentration. The residue was separated by column chromatography to obtain 16.9 g (yield: 58%) of yellowish brown solid Intermediate 4.

Synthesis of Compound 11

10.7 g (30.0 mmol) of Intermediate 4, 15.5 g (36 mmol) of Intermediate 2, 4.3 g (45.0 mmol) of NaOt-Bu, 1.4 g (1.5 mmol) of Pd$_2$(dba)$_3$, and 0.72 g (1.5 mmol) of 2-dicyclohexyl phosphino-2',4',6'-triisopropylbiphenyl were dissolved in 100 mL of toluene, and the mixture was maintained at 90° C. for 6 hours in a nitrogen atmosphere. The mixture was cooled to room temperature, and 30 mL of water was added thereto. Then, the mixture was subjected to extraction twice with 200 ml of methylene chloride. An organic layer was collected and dried, followed by filtration and concentration. The residue was separated by column chromatography to obtain 13.3 g (yield: 62%) of light green solid Compound 11. The structure of this compound was identified using HR-MS. (calc.; 716.4130, found; 716.4123), (1H-NMR, 400 MHz, CD2Cl2: δ7.88-6.89 (m, 22H), δ2.43 (s, 3H), δ2.33 (s, 3H), δ1.73 (s, 6H), δ1.34 (s, 9H) 13C-NMR: 141.3, 140.3, 139.2, 138.8, 136.9, 136.0, 135.7, 135.1, 133.4, 133.1, 132.6, 131.2, 131.0, 130.6, 130.2, 129.6, 129.1, 128.6, 128.4, 128.0, 127.6, 125.3, 125.5, 125.1, 124.8, 124.5, 124.3, 123.9, 123.3, 121.9, 121.1, 120.6, 116.5, 115.4, 38.5, 34.4, 31.3, 30.2, 12.8, 11.5.)

Synthesis Example

Synthesis of Compound 43

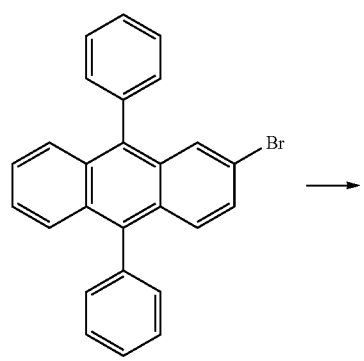

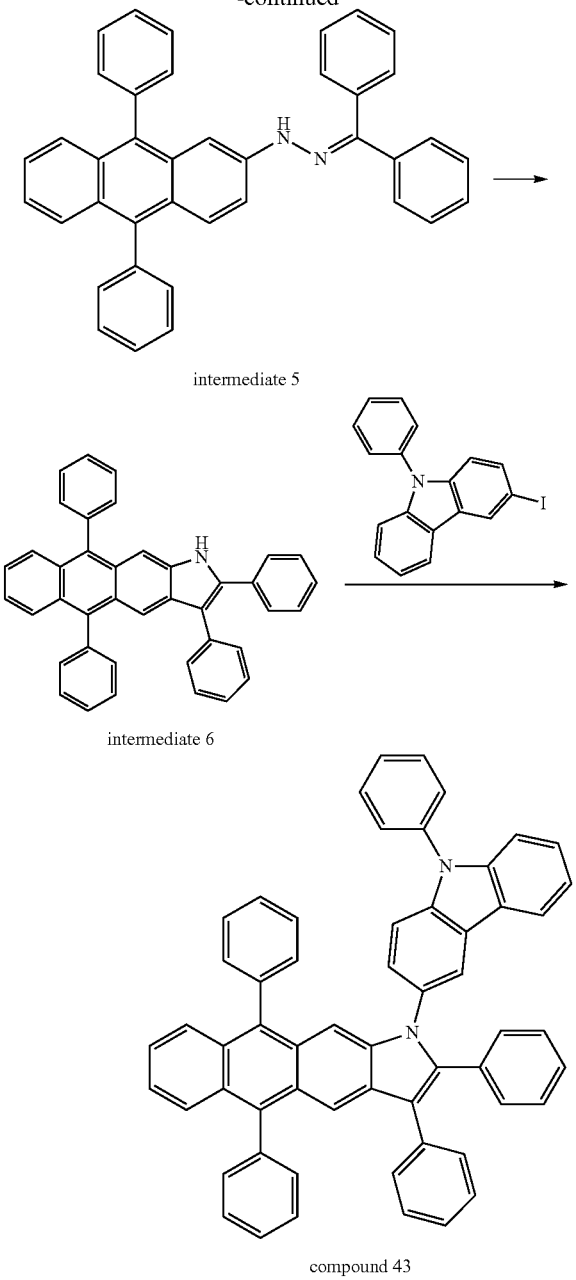

Synthesis of Intermediate 5

Intermediate 5 (44.6 g, yield: 82%) was prepared in the same manner as Intermediate 3, except that 40.9 g (100.0 mmol) of 2-bromo-9,9'-diphenylanthracene was used.

Synthesis of Intermediate 6

41.9 g (80.0 mmol) of Intermediate 5, 30.4 g (160.0 mmol) of p-toluene sulfonic acid, and 40.2 g (160 mmol) of benzylphenylketone were dissolved in a mixed solution of 200 mL of toluene and 50 mL of ethanol, and the mixture was maintained at 100° C. for 12 hours in a nitrogen atmosphere. The mixture was cooled to room temperature, the solvent was concentrated under a reduced pressure, and 100 mL of water was added thereto. Then, the mixture was subjected to extraction twice with 200 ml of methylene chloride. An organic layer was collected and dried, followed by filtration and concentration. The residue was separated by column chromatography to obtain 25.0 g (yield: 60%) of yellowish brown solid Intermediate 6.

Synthesis of Compound 43

Compound 43 (14.2 g, yield: 62%) was prepared in the same manner as Compound 11, except that 15.7 g (30.0 mmol) of Intermediate 6 and 3-iodo-N-phenylcarbazole were used. The structure of this compound was identified using HR-MS. (calc.; 762.9357, found; 762.9344), (1H-NMR, 400 MHz, CD2Cl2: δ8.10-7.84 (m, 2H), δ7.68-6.89 (m, 36H), 13C-NMR: 140.3, 140.0, 139.1, 138.8, 137.9, 136.8, 135.7, 135.1, 134.4, 133.8, 132.6, 131.0, 130.6, 130.0, 129.6, 129.0, 128.2, 128.0, 127.2, 127.0, 126.3, 125.5, 125.1, 124.8, 124.5, 124.3, 123.9, 123.3, 121.9, 121.1, 120.6, 120.1, 119.6, 118.5, 118.3, 116.5, 115.4)

Synthesis Example

Synthesis of Compound 56

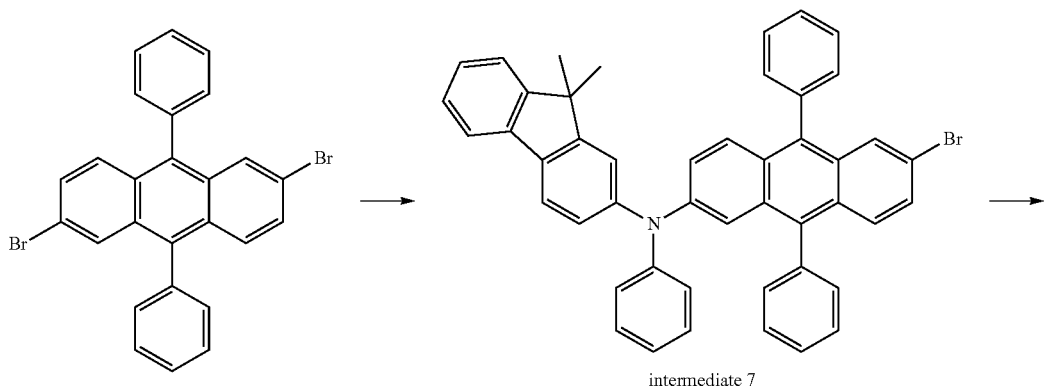

intermediate 7

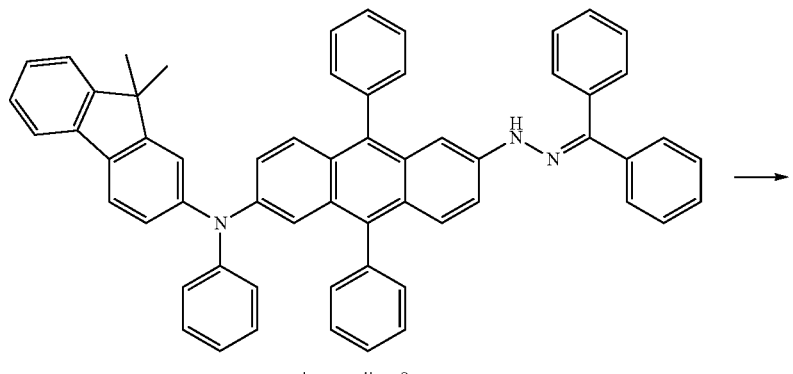

intermediate 8

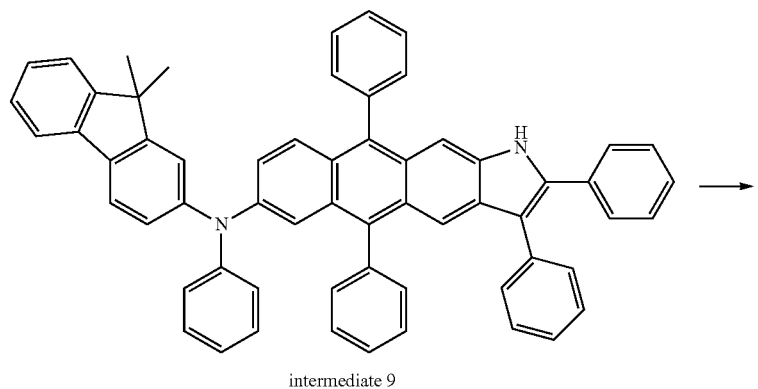

intermediate 9

-continued

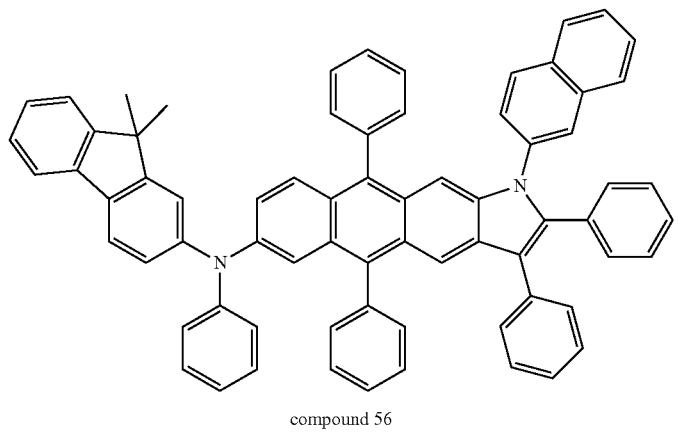

compound 56

Synthesis of Intermediate 7

48.8 g (100.0 mmol) of 2,6-dibromo-9,9'-diphenylanthracene, 8.6 g (30.0 mmol) of Intermediate 1, 4.3 g (45.0 mmol) of NaOt-Bu, 1.4 g (1.5 mmol) of $Pd_2(dba)_3$, and 0.30 g (1.5 mmol) of Pt-$Bu_3$ were dissolved in 200 ml of toluene, and the mixture was maintained at 90° C. for 3 hours in a nitrogen atmosphere. The mixture was cooled to room temperature, and 100 mL of water was added thereto. Then, the mixture was subjected to extraction twice with 300 ml of methylene chloride. An organic layer was collected and dried, followed by filtration and concentration. The residual 2,6-dibromo-9,9'-diphenylanthracene (20.5 g, 42.0 mmol) was collected by filtration, and the residue was separated by column chromatography to obtain 9.4 g (yield: 45%) of light yellow solid Intermediate 7.

Synthesis of Intermediate 8

13.8 g (20.0 mmol) of Intermediate 7, 5.1 g (30 mmol) of benzophenonehydrazone, 2.9 g (30.0 mmol) of NaOt-Bu, 1.4 g (1.5 mmol) of Pd(OAc)$_2$, and 2.4 g (1.5 mmol) of 2-dicyclohexyl phosphino-2',4',6'-triisopropylbiphenyl were dissolved in 80 mL of toluene, and the mixture was maintained at 90° C. for 3 hours in a nitrogen atmosphere. The mixture was cooled to room temperature, and 100 mL of water was added thereto. Then, the mixture was subjected to extraction twice with 300 ml of methylene chloride. An organic layer was collected and dried, followed by filtration and concentration. The residue was separated by column chromatography to obtain 13.7 g (yield: 85%) of yellow solid Intermediate 8.

Synthesis of Intermediate 9

Intermediate 9 (6.2 g, yield: 51% was synthesized in the same manner as Intermediate 6, except that 12.1 g (0.015 mmol) of Intermediate 8 was used.

Synthesis of Compound 56

Compound 56 (6.8 g, yield: 73%) was synthesized in the same manner as Compound 11, except that 8.1 g (10.0 mmol) of Intermediate 9 and 3.1 g (15.0 mmol) of 2-bromonaphthalene were used. The structure of this compound was identified using HR-MS. (calc.; 930.3974, found; 930.3979), (1H-NMR, 400 MHz, CD2Cl2: δ7.98-6.69 (m, 44H), 13C-NMR: 140.1, 140.0, 139.1, 138.9, 138.5, 137.4, 137.1, 136.3, 135.2, 135.1, 134.7, 134.4, 133.8, 133.4, 132.9, 132.6, 131.8, 131.0, 130.6, 130.0, 129.6, 129.0, 128.6, 128.4, 128.2, 128.0, 127.2, 127.0, 126.3, 125.5, 125.1, 124.8, 124.5, 124.3, 123.9, 123.3, 122.8, 122.2, 121.9, 121.1, 120.6, 120.1, 119.6, 118.5, 118.3, 116.5, 115.4)

Synthesis Example

Synthesis of Compound 74

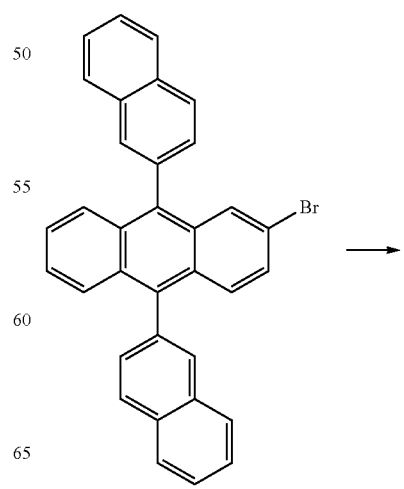

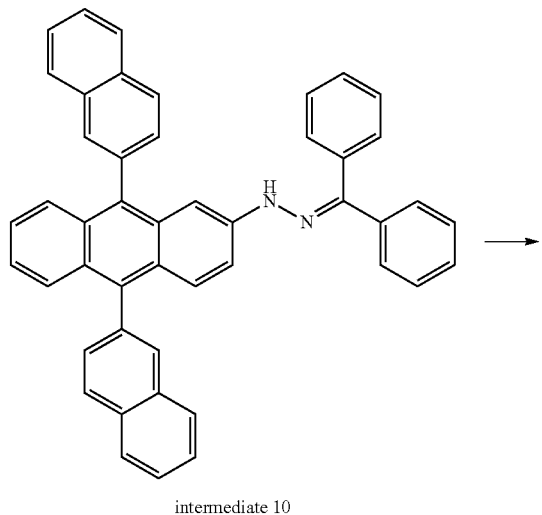

intermediate 10

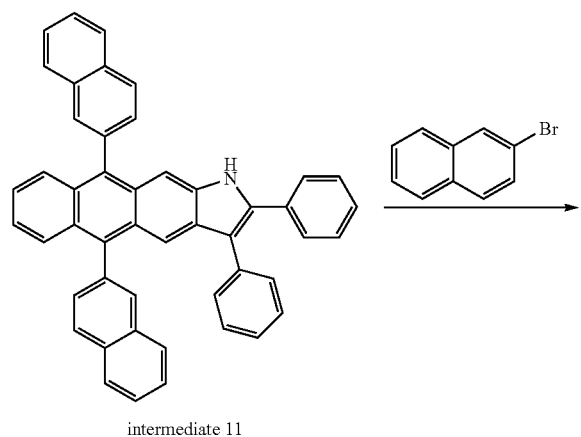

intermediate 11

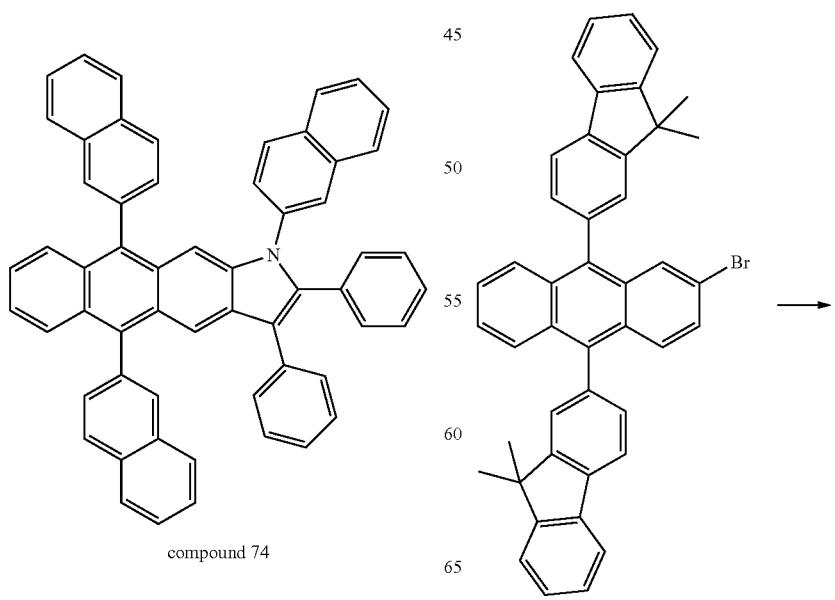

compound 74

Synthesis of Intermediate 10

Intermediate 10 (46.9 g, yield: 75%) was synthesized in the same manner as Intermediate 3, except that 51.0 g (100.0 mmol) of 2-bromo-9,9'-di-2-naphthylanthracene was used.

Synthesis of Intermediate 11

Intermediate 11 (16.5 g, yield: 54%) was synthesized in the same manner as Intermediate 6, except that 31.2 g (50.0 mmol) of Intermediate 10 was used.

Synthesis of Compound 74

Compound 74 (9.0 g, yield: 60%) was synthesized in the same manner as Compound 11, except that 12.4 g (20.0 mmol) of Intermediate 11 and 6.2 g (30.0 mmol) of 2-bromonaphthalene were used. The structure of this compound was identified using HR-MS. (calc.; 747.2926, found; 747.2915), (1H-NMR, 400 MHz, CD2Cl2: δ7.90-7.02 (m, 37H), 13C-NMR: 140.4, 140.2, 139.7, 138.9, 138.3, 137.6, 137.5, 137.3, 135.2, 135.1, 134.7, 134.4, 133.7, 133.3, 132.9, 132.3, 131.8, 131.5, 130.7, 130.0, 129.3, 129.0, 128.6, 128.4, 128.2, 128.0, 127.6, 127.0, 126.3, 125.5, 125.1, 124.8, 124.5, 124.3, 123.9, 122.8, 122.2, 121.9, 120.6, 119.6, 118.5, 118.3)

Synthesis Example

Synthesis of Compound 82

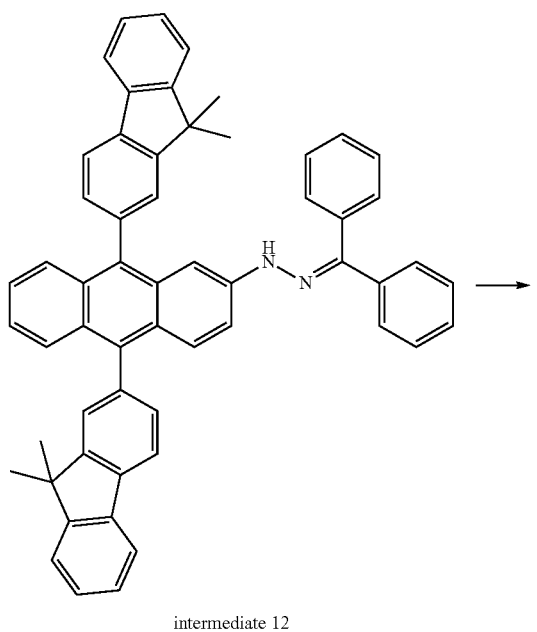

intermediate 12

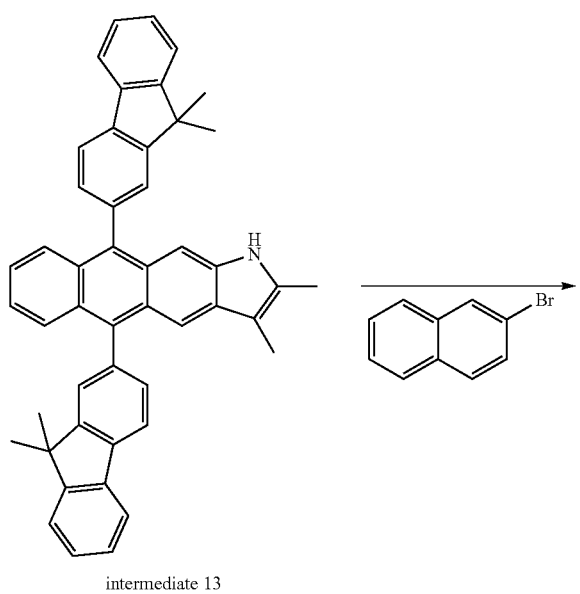

intermediate 13

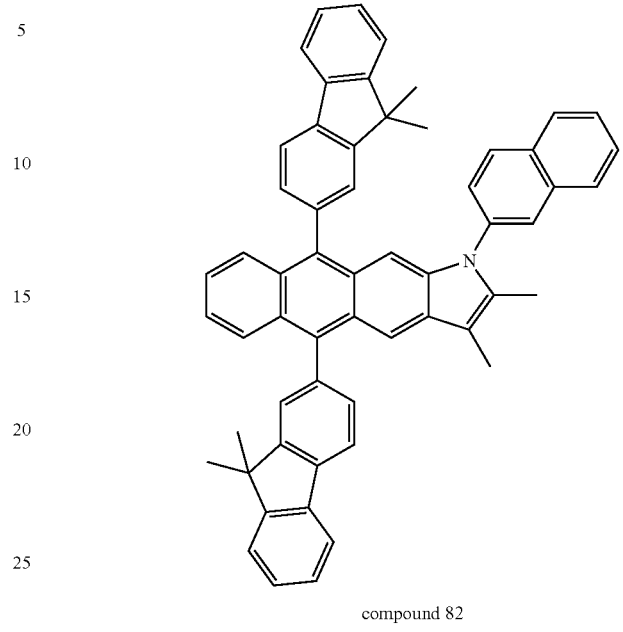

compound 82

Synthesis of Intermediate 12

Intermediate 12 (59.0 g, yield: 78%) was synthesized in the same manner as Intermediate 3, except that 64.1 g (100.0 mmol) of 2-bromo-9,9'-di-9,9-dimethylfluorenylanthracene was used was used.

Synthesis of Intermediate 13

Intermediate 13 (26.5 g, yield: 60%) was synthesized in the same manner as Intermediate 4, except that 53.0 g (70.0 mmol) of Intermediate 12 was used.

Synthesis of Compound 82

Compound 82 (9.9 g, yield: 66%) was synthesized in the same manner as Compound 74, except that 12.6 g (20.0 mmol) of Intermediate 13 was used. The structure of this compound was identified using HR-MS. (calc.; 755.3552, found; 755.3545), (1H-NMR, 400 MHz, CD2Cl2: δ7.90-7.02 (m, 37H), δ2.43 (s, 3H), δ2.32 (s, 3H), δ1.32 (s, 6H), δ1.28 (s, 6H), 13C-NMR: 141.4, 141.2, 140.5, 140.0, 139.7, 138.6, 138.3, 137.6, 137.3, 136.5, 136.1, 135.2, 135.1, 134.7, 134.4, 133.7, 133.3, 132.9, 132.3, 131.8, 131.5, 130.7, 130.0, 129.3, 129.0, 128.6, 128.4, 128.2, 128.0, 127.6, 127.0, 126.6, 125.5, 125.2, 124.8, 124.6, 124.4, 123.2, 122.2, 120.6, 119.6, 118.5, 26.5, 26.3, 18.4, 18.2, 13.2, 13.1)

Synthesis Example

Synthesis of Compound 29

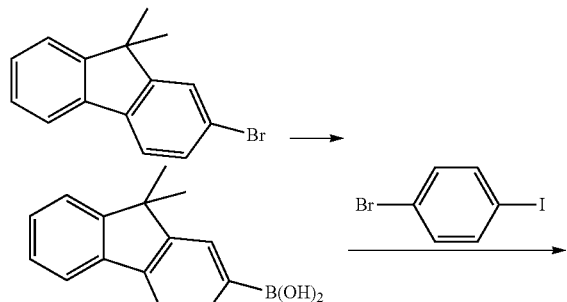

intermediate 14

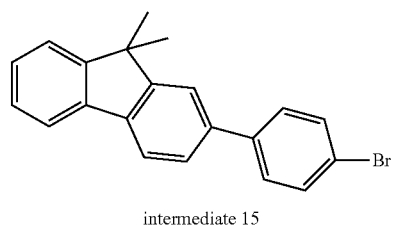

intermediate 15

Synthesis of Intermediate 14

27.3 g (100.0 mmol) of 2-bromo-9,9-dimethylfluorene was dissolved in 200 mL of THF, the solution was cooled to −78° C., and 44 mL (2.5 M in hexane, 110 mmol) of butyl lithium was slowly dropwise added to the solution in a nitrogen atmosphere. The reaction temperature was maintained at −78° C. for 30 minutes, raised to −30° C. and cooled again to −78° C. Then, 16.8 mL (150 mmol) of trimethylborate was slowly dropwise added to the reaction product, and the temperature was raised to room temperature and maintained for 2 hours. 50 mL of 1 N HCl solution was slowly dropwise added to the reaction mixture and maintained for 30 minutes. 100 mL of water was further added to the reaction mixture, and the reaction mixture was subjected to extraction twice with 200 ml of ethylacetate. An organic layer was collected and dried, followed by filtration and concentration. The residue was separated by column chromatography to obtain 16.4 g (yield: 69%) of white solid Intermediate 14.

Synthesis of Intermediate 15

11.9 g (50.0 mmol) of Intermediate 14, 28.3 g (100.0 mmol) of bromoiodobenzene, 3.5 g (3.0 mmol) of Pd(PPh$_3$)$_4$, and 8.0 g (200 mmol) of NaOH were dissolved in a mixed solution of 150 mL of THF and 50 mL of water, and the mixture was maintained at 70° C. for 12 hours. The mixture was cooled to room temperature, and 100 mL of water was added thereto. Then, the mixture was subjected to extraction twice with 200 ml of methylene chloride. An organic layer was collected and dried, followed by filtration and concentration. The residue was separated by column chromatography to obtain 11.4 g (yield: 64%) of white solid Intermediate 15.

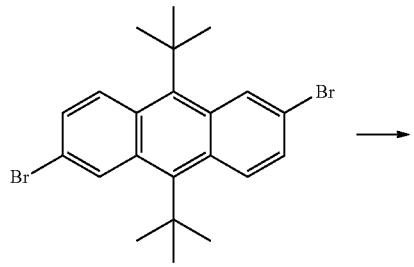

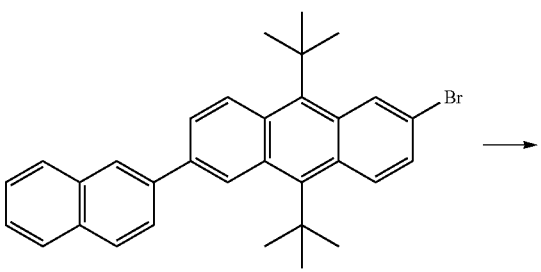

intermediate 16

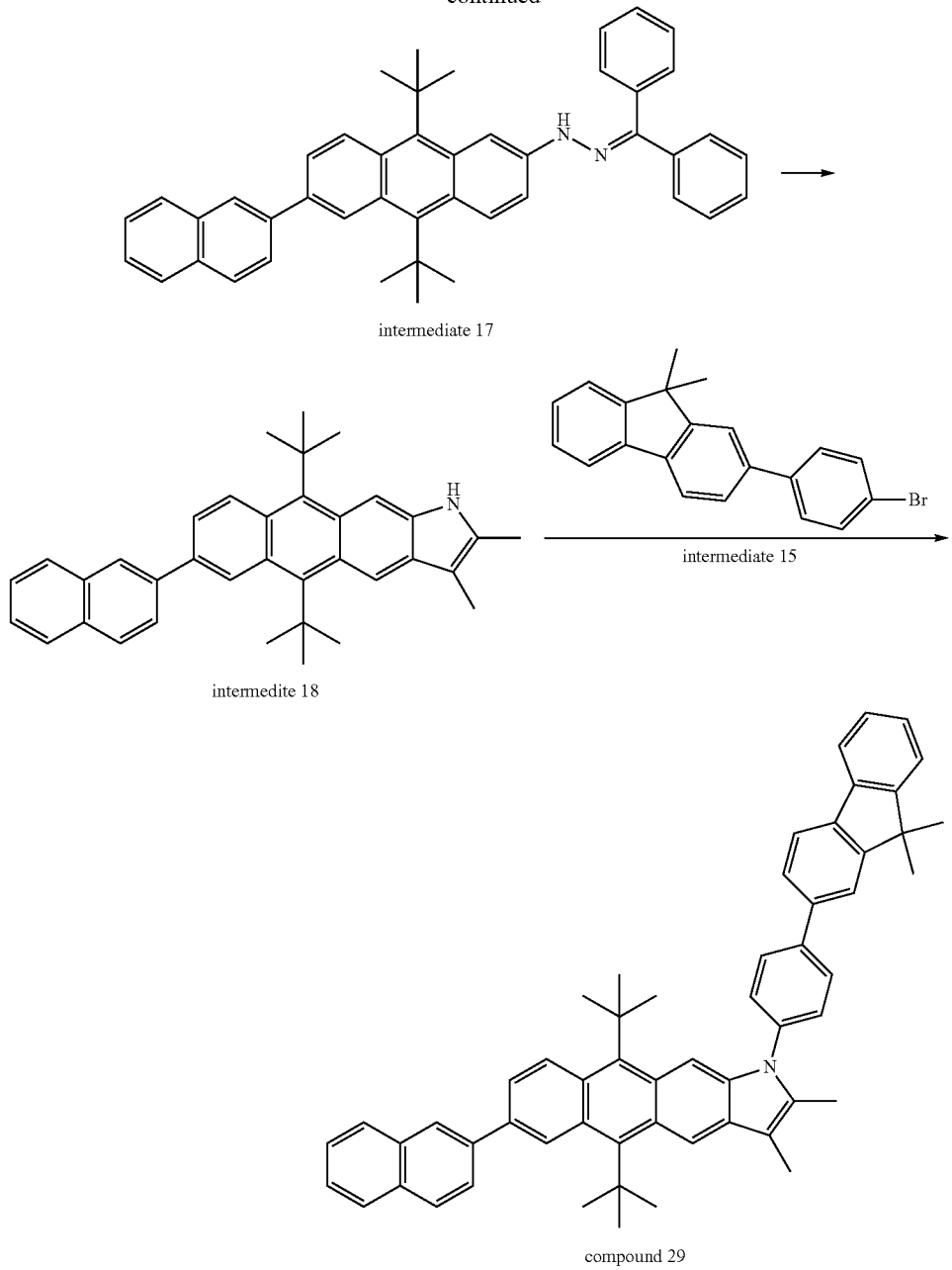

Synthesis of Intermediate 16

44.8 g (100.0 mmol) of 2,6-dibromo-9,9'-di-t-butylanthracene, 3.4 g (20 mmol) of 2-naphthylboronic acid, 1.2 g (1.0 mmol) of Pd(PPh$_3$)$_4$, and 3.2 g (80 mmol) of NaOH were dissolved in a mixed solution of 150 mL of THF and 50 mL of water, and the mixture was maintained at 70° C. for 12 hours. The mixture was cooled to room temperature, and 100 mL of water was added thereto. Then, the mixture was subjected to extraction twice with 200 ml of methylene chloride. An organic layer was collected and dried, followed by filtration and concentration. The residual 2,6-dibromo-9,9'-di-t-butylanthracene (22.4 g, 50.0 mmol) was separated by column chromatography and recrystallization to obtain 6.1 g (yield: 61%) of light yellow solid Intermediate 16.

Synthesis of Intermediate 17

Intermediate 17 (6.2 g, yield: 84%) was synthesized in the same manner as Intermediate 3, except that 5.9 g (12.0 mmol) of Intermediate 16 was used.

Synthesis of Intermediate 18

Intermediate 18 (2.9 g, yield: 67%) was synthesized in the same manner as Intermediate 4, except that 5.5 g (9.0 mmol) of Intermediate 17 was used.

Synthesis of Compound 29

Compound 29 (3.2 g, yield: 70%) was synthesized in the same manner as Compound 11, except that 2.9 g (6.0 mmol)

of Intermediate 18 and 3.1 g (9.0 mmol) of Intermediate 15 were used. The structure of this compound was identified using HR-MS. (calc.; 751.4178, found; 71.4169), (1H-NMR, 400 MHz, CD2Cl2: δ8.02-7.02 (m, 23H), δ2.43 (s, 3H), δ2.32 (s, 3H), δ1.62 (s, 6H), δ1.47 (s, 9H), δ1.45 (s, 9H) 13C-NMR: 140.5, 140.1, 139.4, 138.6, 138.4, 137.6, 137.0, 136.7, 136.2, 135.2, 135.1, 134.8, 134.4, 133.7, 133.3, 132.9, 132.3, 131.8, 131.5, 130.3, 130.0, 129.3, 129.0, 128.6, 128.4, 128.2, 128.0, 127.6, 127.0, 126.8, 125.6, 125.2, 124.9, 124.6, 124.4, 122.2, 120.6, 119.6, 118.5, 26.6, 26.3, 18.4, 18.2, 13.2, 13.1)

Example 1

An anode was prepared by cutting a Corning 15 Ωcm² (1200 Å) ITO glass substrate to a size of 50 mm×50 mm×0.7 mm, ultrasonically cleaning the glass substrate using isopropyl alcohol and pure water for 5 minutes each, and then irradiating with UV light for 30 minutes and exposing to ozone to clean. Then, the anode was mounted in a vacuum deposition apparatus.

Then, 2-TNATA as an HIL material was vacuum-deposited on the glass substrate to form a HIL having a thickness of 600 Å. Then, 4,4'-bis[N-(1-naphthyl)-N-phenylamino]biphenyl (NPB) as a hole transport compound was vacuum deposited on the HIL to form a HTL having a thickness of 300 Å.

9,10-di-naphthalene-2-yl-anthracene (ADN) as a blue fluorescent host and Compound 11 as a blue fluorescent dopant were simultaneously deposited at a weight ratio of 98:2 on the HTL to form an EML having a thickness of 300 Å.

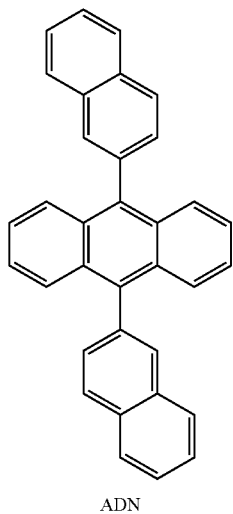 [SMILES: c1ccc2cc(-c3c4ccccc4c(-c4ccc5ccccc5c4)c4ccccc34)ccc2c1]

ADN

Then, Alq₃ was deposited on the EML to form an ETL having a thickness of 300 Å, and then LiF (a halogenated alkali metal) was deposited on the ETL to form an EIL having a thickness of 10 Å. Then, Al was deposited on the EIL to a thickness of 3000 Å (cathode), thereby forming a LiF/Al electrode. As a result, the manufacture of an organic light-emitting device was completed.

Example 2

An organic light-emitting device was manufactured in the same manner as Example 1, except that Compound 29 was used instead of Compound 11 to form the EML.

Example 3

An organic light-emitting device was manufactured in the same manner as Example 1, except that Compound 43 was used instead of Compound 11 to form the EML.

Example 4

An organic light-emitting device was manufactured in the same manner as Example 1, except that Compound 56 was used instead of Compound 11 to form the EML.

Example 5

An organic light-emitting device was manufactured in the same manner as Example 1, except that Compound 74 was used instead of Compound 11 to form the EML.

Example 6

An organic light-emitting device was manufactured in the same manner as Example 1, except that Compound 82 was used instead of Compound 11 to form the EML.

Example 7

An organic light-emitting device was manufactured in the same manner as Example 1, except that Compound 82 was used instead of Alq₃ to form the ETL.

Comparative Example 1

An organic light-emitting device was manufactured in the same manner as Example 1, except that 1,4-bis-(2,2-diphenylvinyl)biphenyl) (DPVBi) was used as a blue fluorescent dopant instead of Compound 11 to form the EML.

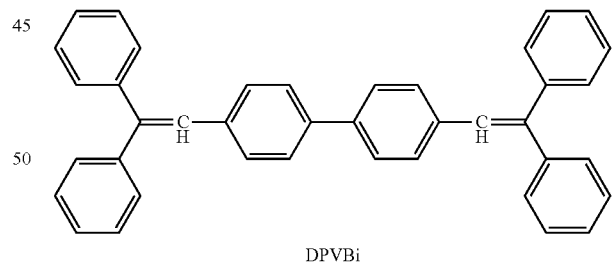

DPVBi

The organic light-emitting devices manufactured using the heterocyclic compounds of Formula 1 according to embodiments of the present invention had driving voltages that were lower by 1 V or greater than the device using DPVBi, and thus had higher efficiency and good I-V-L characteristics. In particular, lifetime characteristics were markedly improved by 100% or greater in the organic light-emitting devices according to Examples 1 through 7 as compared to the organic light-emitting device according to Comparative Example 1. The results are shown in Table 1 below.

TABLE 1

|  | Emitting material or electron transporting material | Driving voltage | Current density | Brightness | light-emission efficiency (cd/A) | Emitted color | Half-life span (hr @ 100 mA/cm$^2$) |
|---|---|---|---|---|---|---|---|
| Example 1 | Compound 11 | 6.27 | 50 | 2,850 | 5.70 | blue | 238 hr |
| Example 2 | Compound 29 | 6.13 | 50 | 3,045 | 6.09 | blue | 241 hr |
| Example 3 | Compound 43 | 6.30 | 50 | 2,910 | 5.82 | blue | 268 hr |
| Example 4 | Compound 56 | 6.41 | 50 | 3,520 | 7.04 | blue green | 275 hr |
| Example 5 | Compound 74 | 6.33 | 50 | 3,372 | 6.74 | blue green | 288 hr |
| Example 6 | Compound 82 | 6.14 | 50 | 3,070 | 6.14 | blue | 283 hr |
| Example 7 | Compound 82 | 5.75 | 50 | 3,470 | 6.94 | blue | 345 hr |
| Comparative Example 1 | DPVBi | 7.85 | 50 | 1,560 | 3.12 | blue | 113 hr |

The heterocyclic compounds according to embodiments of the present invention have good electrical characteristics, charge transporting capabilities, and light-emitting characteristics, high glass transition temperatures (Tg), and crystallization prevention characteristics. Thus, the heterocyclic compounds may be used as electron transporting materials for all-color fluorescent and phosphorescent devices, such as red, green, blue, and white fluorescent and phosphorescent devices, or as an emitting material for green, blue, and white fluorescent and phosphorescent devices. Thus, organic light-emitting devices having high efficiency, low driving voltages, high brightness and long lifespans may be manufactured using the heterocylic compounds.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heterocyclic compound comprising a compound represented by Formula 1 below:

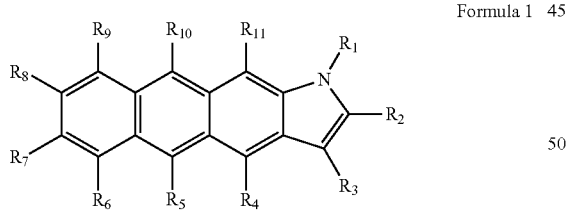

Formula 1 wherein each of $R_1$ through $R_{11}$ is independently selected from the group consisting of hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $C_5$-$C_{50}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups, wherein two or more neighboring substituents selected from $R_1$ through $R_{11}$ may optionally combine to form an aromatic ring, and wherein at least one of $R_1$ or $R_7$ is independently selected from the group consisting of heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $C_5$-$C_{50}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups.

2. The heterocyclic compound of claim 1, wherein $R_1$ is selected from the group consisting of:

unsubstituted monocyclic to tricyclic aryl groups selected from the group consisting of phenyl groups, naphthyl groups, biphenyl groups, terphenyl groups, anthracenyl groups, fluorenyl groups, and carbazolyl groups; and substituted monocyclic to tricyclic aryl group selected from the group consisting of phenyl groups, naphthyl groups, biphenyl groups, terphenyl groups, anthracenyl groups, fluorenyl groups, and carbazolyl groups substituted with at least one substituent selected from the group consisting of $C_1$-$C_5$ alkyl groups, $C_1$-$C_5$ alkoxy groups, cyano groups, amine groups, phenoxy groups, phenyl groups and halogen groups.

3. The heterocyclic compound of claim 1, wherein $R_7$ is selected from the group consisting of:

unsubstituted monocyclic to tricyclic aryl groups selected from the group consisting of phenyl groups, naphthyl groups, biphenyl groups, terphenyl groups, anthracenyl groups, fluorenyl groups and carbazolyl groups;

unsubstituted $C_{12}$-$C_{50}$ arylamine groups;

substituted monocyclic to tricyclic aryl group selected from the group consisting of phenyl groups, naphthyl groups, biphenyl groups, terphenyl groups, anthracenyl groups, fluorenyl groups, and carbazolyl groups substituted with at least one substituent selected from the group consisting of $C_1$-$C_5$ alkyl groups, $C_1$-$C_5$ alkoxy groups, cyano groups, amine groups, phenoxy groups, phenyl groups, and halogen groups; and $C_{12}$-$C_{50}$ arylamine groups substituted with at least one substituent selected from the group consisting of $C_1$-$C_5$ alkyl groups, $C_1$-$C_4$ alkoxy groups, cyano groups, amine groups, phenoxy groups, phenyl groups, and halogen groups.

4. The heterocyclic compound of claim 1, wherein each of $R_2$ and $R_3$ is independently selected from the group consisting of methyl groups and phenyl groups.

5. The heterocyclic compound of claim 1, wherein each of $R_5$ and $R_{10}$ is independently selected from the group consisting of t-butyl groups, phenyl groups, naphthyl groups, and fluorenyl groups.

6. The heterocyclic compound of claim 1, wherein the compound represented by Formula 1 comprises a compound selected from the group consisting of Compounds 11, 29, 43, 56, 74 and 82:

11

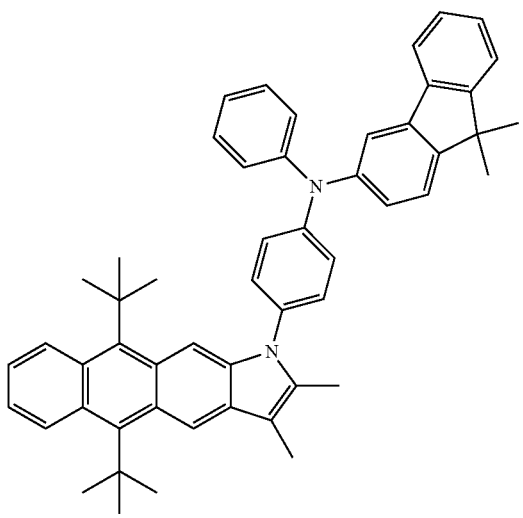

29

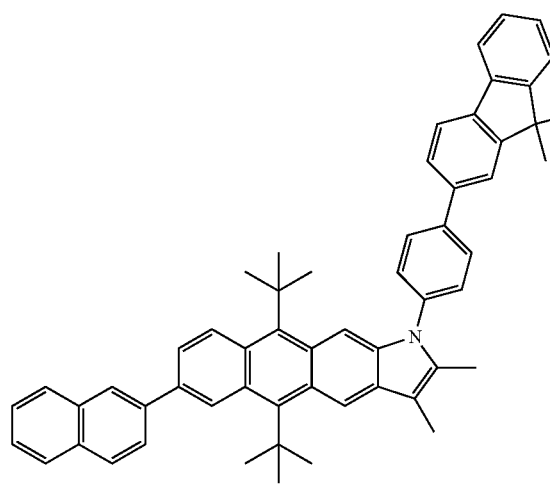

-continued

43

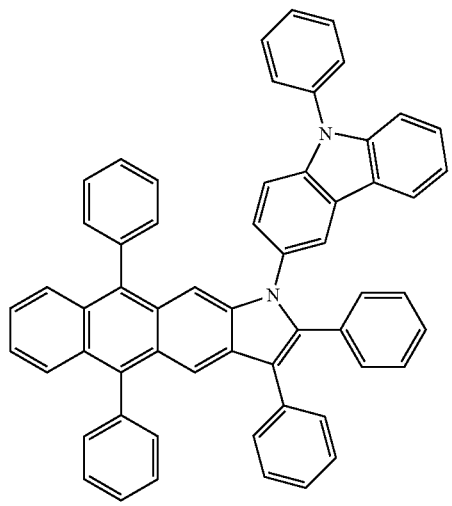

56

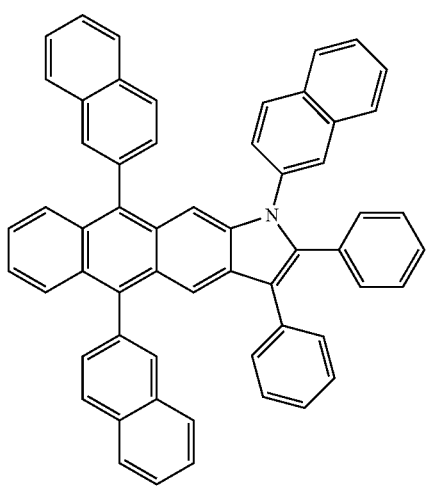

74

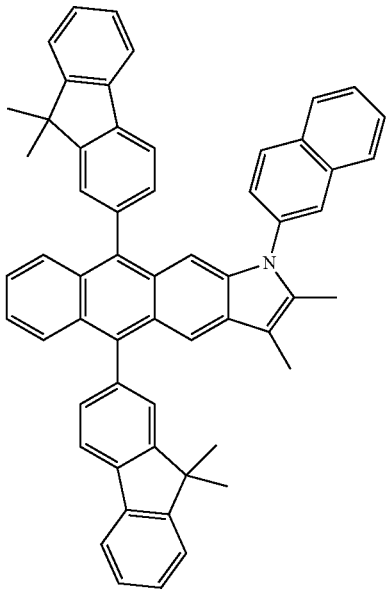

7. An organic light-emitting device comprising:
a first electrode;
a second electrode; and
an organic layer between the first electrode and the second electrode,
wherein the organic layer comprises the heterocyclic compound of claim 1.

8. The organic light-emitting device of claim 7, wherein the organic layer comprises an electron injection layer or an electron transport layer.

9. The organic light-emitting device of claim 7, wherein the organic layer comprises a single layer having both electron injection and electron transport capabilities.

10. The organic light-emitting device of claim 7, wherein the organic layer comprises an emission layer.

11. The organic light-emitting device of claim 7, wherein the organic layer comprises an emission layer, and the heterocyclic compound is a host for the emission layer of a fluorescent or phosphorescent device.

12. The organic light-emitting device of claim 7, wherein the organic layer comprises an emission layer, and the heterocyclic compound is a fluorescent dopant of the emission layer.

13. The organic light-emitting device of claim 7, wherein the organic layer comprises an emission layer, and an electron injection layer or an electron transport layer, wherein the emission layer comprises an anthracene compound or an arylamine compound or a styryl compound.

14. The organic light-emitting device of claim 7, wherein the organic layer comprises an emission layer, and an electron injection layer or an electron transport layer, wherein the emission layer comprises a red emission layer, a green emission layer, a blue emission layer or a white emission layer that comprises a phosphorescent compound.

15. The organic light-emitting device of claim 7, wherein the organic layer comprises at least one layer selected from the group consisting of a hole injection layer, a hole transport layer, an electron blocking layer, an emission layer, a hole blocking layer, an electron transport layer, and an electron injection layer.

16. The organic light-emitting device of claim 15, wherein the organic light-emitting device comprises a first electrode/hole injection layer/emission layer/second electrode structure, or a first electrode/hole injection layer/hole transport layer/emission layer/electron transport layer/second electrode structure, or a first electrode/hole injection layer/hole transport layer/emission layer/electron transport layer/electron injection layer/second electrode layer structure.

17. A flat panel display device, comprising the organic light-emitting device of claim 7, wherein the first electrode of the organic light-emitting device is electrically connected to a source electrode or a drain electrode of a thin-film transistor.

18. An organic light-emitting device comprising:
a first electrode;
a second electrode; and
an organic layer between the first electrode and the second electrode,
wherein the organic layer comprises at least one layer comprising the heterocyclic compound of claim 1, the at least one layer being formed using a wet process.

* * * * *